US010426668B2

(12) United States Patent
Maeda et al.

(10) Patent No.: US 10,426,668 B2
(45) Date of Patent: Oct. 1, 2019

(54) BINOCULAR DISPLAY APPARATUS

(71) Applicant: Rohm Co., Ltd., Kyoto (JP)

(72) Inventors: Toshihisa Maeda, Kyoto (JP); Daisuke Nishinohara, Kyoto (JP); Masahide Tanaka, Osaka (JP)

(73) Assignee: Rohm Co., Ltd., Kyoto (JP)

( * ) Notice: Subject to any disclaimer, the term of this patent is extended or adjusted under 35 U.S.C. 154(b) by 90 days.

(21) Appl. No.: 15/508,655

(22) PCT Filed: Sep. 14, 2015

(86) PCT No.: PCT/JP2015/076051
§ 371 (c)(1),
(2) Date: Mar. 3, 2017

(87) PCT Pub. No.: WO2016/043165
PCT Pub. Date: Mar. 24, 2016

(65) Prior Publication Data
US 2017/0252216 A1 Sep. 7, 2017

(30) Foreign Application Priority Data

Sep. 18, 2014 (JP) ................................ 2014-190160
Oct. 21, 2014 (JP) ................................ 2014-214474
Aug. 11, 2015 (JP) ................................ 2015-159111

(51) Int. Cl.
*H04N 7/18* (2006.01)
*A61F 9/08* (2006.01)
(Continued)

(52) U.S. Cl.
CPC ................. *A61F 9/08* (2013.01); *G06T 3/20* (2013.01); *G06T 3/40* (2013.01); *H04N 13/139* (2018.05);
(Continued)

(58) Field of Classification Search
CPC .......... A61F 9/08; H04N 7/18; H04N 13/383; H04N 13/344; H04N 13/139;
(Continued)

(56) References Cited

U.S. PATENT DOCUMENTS 6,177,952 B1    1/2001  Tabata et al.
9,558,719 B2 *  1/2017  Matsushima .......... G09G 5/377
(Continued)

FOREIGN PATENT DOCUMENTS

JP      07-087422       3/1995
JP      H11180011 A     7/1999
(Continued)

OTHER PUBLICATIONS

Japan Patent Office, International Search Report for PCT/JP2015/076051 dated Nov. 24, 2015 (with English translation).
(Continued)

*Primary Examiner* — Trang U Tran
(74) *Attorney, Agent, or Firm* — Fish & Richardson P.C.

(57) ABSTRACT

A binocular display system comprises: a binocular image pickup system that includes a right eye-use image pickup optical system and a left eye-use image pickup optical system; a binocular display system that includes a right eye-use display unit which displays image information picked up by the right eye-use image pickup optical system, and a left eye-use display unit which displays image information picked up by the left eye-use image pickup optical system; and a correlating means that correlates the binocular image pickup system and the binocular image display system. In addition, a binocular display device comprises an image processing unit that processes the image information obtained by the binocular image pickup system. The image processing unit can enlarge an image and display the same on the binocular display system, and correct the movement (Continued)

of the displayed image when at least a prescribed amount of enlargement is carried out.

14 Claims, 22 Drawing Sheets

(51) Int. Cl.
*H04N 13/344* (2018.01)
*H04N 13/139* (2018.01)
*H04N 13/398* (2018.01)
*G06T 3/20* (2006.01)
*G06T 3/40* (2006.01)

(52) U.S. Cl.
CPC ......... *H04N 13/344* (2018.05); *H04N 13/398* (2018.05); *H04N 2213/008* (2013.01)

(58) Field of Classification Search
CPC ............... H04N 13/239; H04N 13/398; H04N 2213/008; G02B 27/02; G06T 3/20; G06T 3/40
USPC ................ 348/63, 42, 43, 61–62, 115, 222.1
See application file for complete search history.

(56) References Cited

U.S. PATENT DOCUMENTS

| | | | |
|---|---|---|---|
| 9,699,441 B2 * | 7/2017 | Inaba | ................ G02B 7/102 |
| 2005/0168569 A1 | 8/2005 | Igarashi et al. | |
| 2009/0273688 A1 | 11/2009 | Nonaka et al. | |
| 2010/0013739 A1 | 1/2010 | Sako et al. | |
| 2012/0218425 A1 | 8/2012 | Nonaka et al. | |
| 2013/0009868 A1 | 1/2013 | Sako et al. | |
| 2014/0085446 A1 | 3/2014 | Hicks | |
| 2014/0347510 A1 | 11/2014 | Nonaka et al. | |
| 2014/0375559 A1 | 12/2014 | Sako et al. | |
| 2015/0293362 A1 | 10/2015 | Takahashi et al. | |
| 2016/0124503 A1 | 5/2016 | Sako et al. | |
| 2016/0198137 A1 | 7/2016 | Nonaka et al. | |
| 2017/0315610 A1 | 11/2017 | Sako et al. | |

FOREIGN PATENT DOCUMENTS

| | | | |
|---|---|---|---|
| JP | 2003-287708 | 10/2003 | |
| JP | 2005172851 A | 6/2005 | |
| JP | 2006135884 A | 5/2006 | |
| JP | 2006-208997 | 8/2006 | |
| JP | 2008-065169 | 3/2008 | |
| JP | 2008191724 A | 8/2008 | |
| JP | 2009-222921 | 10/2009 | |
| JP | 2010-004113 | 1/2010 | |
| JP | 2010-016613 | 1/2010 | |
| JP | 2010-124191 A * | 3/2010 | ............. H04N 13/04 |
| JP | 2010-124191 | 6/2010 | |
| JP | 4600290 | 12/2010 | |
| JP | 2014-011624 | 1/2014 | |
| JP | 2014508596 A | 4/2014 | |
| JP | 2014/077046 | 1/2017 | |

OTHER PUBLICATIONS

Japanese Patent Office, Office action in JP application No. 2014-214474 (dated Aug. 7. 2018) (with English translation).
Japanese Patent Office, Office action in JP application No. 2014-190160 (dated Sep. 11, 2018) (with English translation).
Japanese Patent Office, Office action in JP application No. 2014-214474 (dated Feb. 19, 2019) (with English translation).

* cited by examiner

BINOCULAR DISPLAY APPARATUS

TECHNICAL FIELD

The present invention relates to a binocular display apparatus.

BACKGROUND ART

Various studies have been done on binocular display apparatuses and their applications. For example, their applications as vision aid systems for the visually impaired have been studied. Common causes of vision disorders include eye diseases, such as glaucoma, cataract, night blindness, and age-related macular degeneration, and developmental disorders, such as vision disorders in childhood. As remedies, various aid cameras and aid displays have been proposed. In this context, binocular display apparatuses are employed as aid displays. As one example, there is proposed a goggle-type vision enhancement device in which an image in a region corresponding to a user's visual field out of a picture taken with a CCD camera is subjected to image processing for viewing by the user through a virtual-image display device (Patent Document 1). For another example, there is proposed a configuration in which image information obtained from an imager is processed to be displayed in a display area on a display such that, on the display, a user can see the processed image in the display area simultaneously with an image of the outside world (Patent Document 2).

LIST OF CITATIONS

Patent Literature

Patent Document 1: Japanese Patent Application published as No. 2003-287708
Patent Document 2: Japanese Patent No. 4600290

SUMMARY OF THE INVENTION

Technical Problem

However, conventional binocular display apparatuses leave much room for further studies.

Against the background given above, it is an object of the present invention to propose more useful binocular display apparatuses.

Means for Solving the Problem

According to one aspect of what is disclosed herein, a binocular display apparatus includes: a binocular imaging system including a right-eye imaging optical system and a left-eye imaging optical system; a binocular display system including a right-eye display configured to display image information taken by the right-eye imaging optical system and a left-eye display configured to display image information taken by the left-eye imaging optical system; and correlating means for establishing a correlation between the binocular imaging system and the binocular display system. The correlating means may establish the correlation such that, when a subject taken by the binocular imaging system is displayed by the binocular display system, the convergence angle between right and left eyes seeing the subject displayed by the binocular display system is approximate to the convergence angle observed when the right and left eye really see the subject. The optical axes of the right-eye and left-eye imaging optical systems may be parallel to each other, and the correlating means may establish the correlation such that the optical axis interval between the right-eye and left-eye displays is equivalent to the optical axis interval between the right-eye and left-eye imaging optical systems.

The binocular display system may be configured to provide a display virtual image at a distance equivalent to the standard subject distance of the binocular imaging system. The binocular display system may have a dioptric power adjusting function. The binocular display system may have at least one of an image enlarging function and an image reducing function.

The optical axes of the right-eye and left-eye imaging optical systems may be parallel to each other, the optical axis interval of the binocular display system may differ from the optical axis interval of the binocular imaging system, and the correlating means may have an image shifting function based on the difference between the optical axis interval of the binocular imaging system and the optical axis interval of the binocular display system. The binocular display system may have an optical axis interval adjusting function, and the correlating means may have an image shifting function based on optical axis interval adjustment in the binocular display system. The optical axes of the right-eye and left-eye imaging optical systems may be parallel to each other, the binocular display system may have a display optical system different from the imaging optical systems of the binocular imaging system, and the correlating means may have an image shifting function based on the difference between the imaging optical system and the display optical system.

The optical axis of the binocular imaging system and the optical axis of the binocular display system may coincide with each other. The binocular display apparatus may further include: an image processor configured to process the image information from the binocular imaging system; and a memory configured to store preset information on correction in the image processor. The preset information may be stored separately for the right and left eyes.

The binocular display apparatus may further include: an image processor configured to be capable of displaying the image information from the binocular imaging system through the binocular display system on an enlarged scale and to correct movement of the displayed image when enlargement higher than a predetermined magnification is performed. The binocular display apparatus may further include: a circumstance sensor configured to detect the circumstances of use; and a controller configured to stop the binocular display system from changing display when the circumstance sensor detects minute vibrations.

According to another aspect of what is disclosed herein, a binocular display apparatus includes: a binocular imaging system including a right-eye imaging optical system and a left-eye imaging optical system; an image processor configured to process image information obtained by the binocular imaging system; and a binocular display system including a right-eye display and a left-eye display and displaying the image information from the image processor. Here, the image processor is configured to be capable of displaying an image through the binocular display system on an enlarged scale and to correct movement of the displayed image when enlargement higher than a predetermined magnification is performed. The image processor may be configured to correct movement of the displayed image by delaying the movement of the displayed image when enlargement higher than the predetermined magnification is performed. The image processor may be configured to correct movement of the displayed image by reducing the frame rate of image display on the displays when enlargement higher than the predetermined magnification is performed.

According to yet another aspect of what is disclosed herein, a binocular display apparatus includes: a binocular imaging system including a right-eye imaging optical system and a left-eye imaging optical system; an image processor configured to process image information obtained by the binocular imaging system; a binocular display system including a right-eye display and a left-eye display and displaying the image information from the image processor; a circumstance sensor configured to detect the circumstances of use; and a controller configured to stop the binocular display system from changing display when the circumstance sensor detects minute vibrations. The binocular display apparatus may further include: a processing controller configured to automatically change processing by the image processor based on detection by the circumstance sensor. The processing controller may be configured to effect an automatic return of the processing by the image processor to a standard state based on the detection by the circumstance sensor.

Advantageous Effects of the Invention

It is thus possible to provide more useful binocular display apparatuses as described above.

DESCRIPTION OF EMBODIMENTS

EXAMPLE 1

Figure 1:
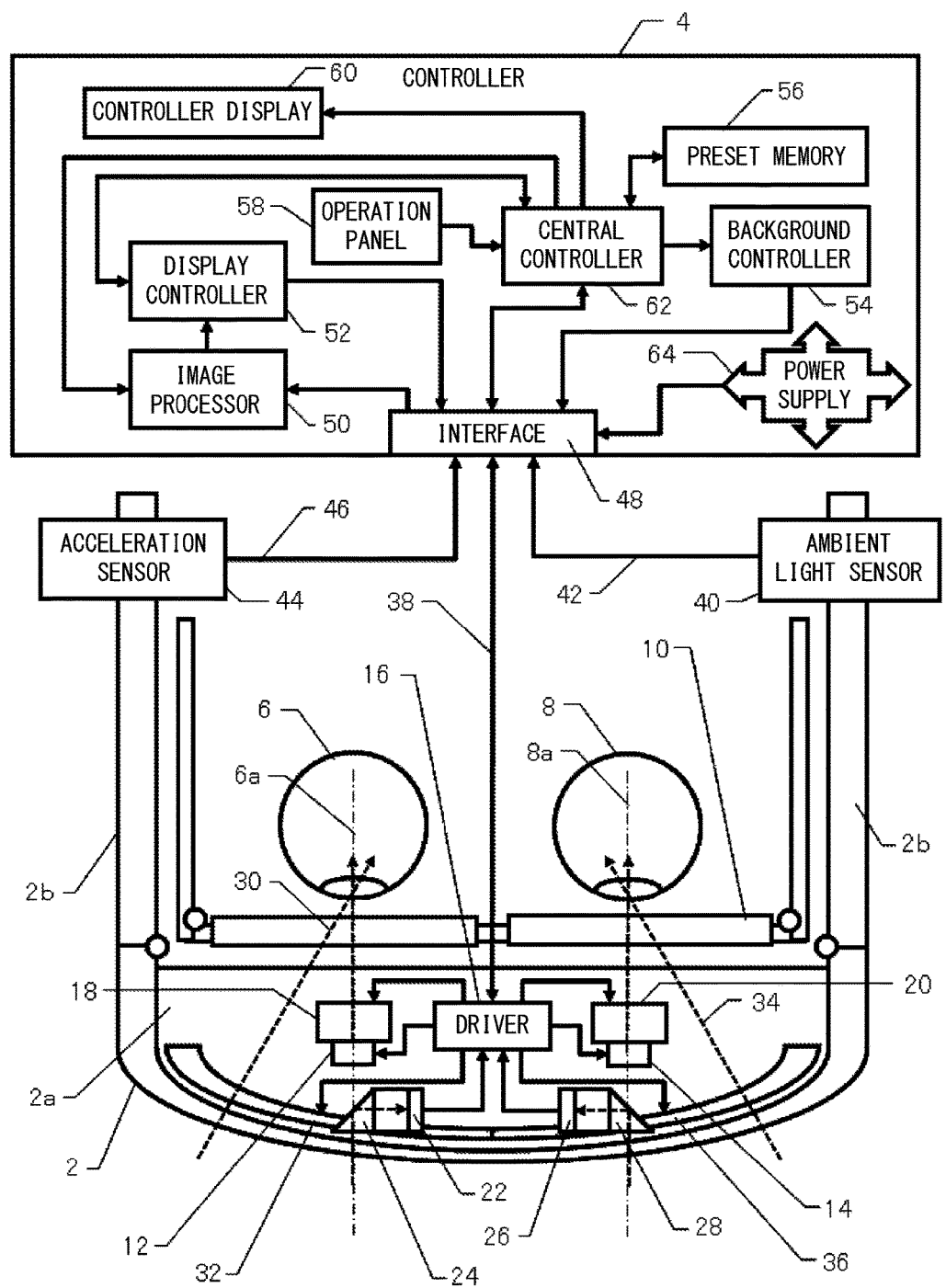
FIG. 1 is a block diagram showing the overall configuration of a vision aid system in Example 1 embodying the present invention (Example 1)

FIG. 1 is a block diagram showing the overall configuration of a vision aid system in Example 1 embodying the present invention. The vision aid system of Example 1 includes a goggle-type head mounted display (hereinafter "HMD") 2 and a controller 4 connected thereto by a cable. The cable includes a parallel data communication line and a power supply line between the HMD 2 and the controller 4.

The HMD 2 is worn in further front of ordinary eyeglasses 10 worn in front of a user's right and left eyes 6 and 8. Thus, the HMD 2 is used on the assumption that the eyeglasses 10 correct any refraction disorder of the user's right and left eyes 6 and 8. To that end, the HMD 2 comprises a body 2a and temples 2b, and is configured such that, when the temples 2b are placed on the ears over the eyeglasses 10, the body 2a is located in front of the lenses of the eyeglasses 10.

Inside the body 2a, the HMD 2 has a right-eye display 12 and a left-eye display 14, which each comprise an OLED (organic light-emitting diode) display panel exploiting organic electroluminescence. As will be described later, a driver 16 drives the right-eye and left-eye displays 12 and 14 individually based on a video signal fed from the controller 4 to display right-eye and left-eye images respectively. As indicated by broken-line arrows, virtual images of the displayed images are directed to the right and left eyes 6 and 8 along lines of sight 6a and 8a by right-eye and left-eye eyepiece optical systems 18 and 20 respectively. Under the control of the controller 4, the driver 16 also performs focus adjustment on the right-eye and left-eye eyepiece optical systems 18 and 20, and moreover performs light-of-sight shift adjustment whereby the optical axes of those optical systems are translated to be displaced from the lines of sight 6a and 8a.

As indicated by a broken-line arrow, a real image of the visual field is imaged on a right-eye image sensor 22 inside the body 2a by a right-eye deflecting zoom lens optical system 24, which deflects light incident along the right-eye line of sight 6a by 90 degrees inward (in the diagram, rightward). Likewise, a real image of the visual field is imaged on a left-eye image sensor 26 by a left-eye deflecting zoom lens optical system 28, which deflects light incident along the left-eye line of sight 8a by 90 degrees inward (in the diagram, leftward). As will be described later, the visual-field images taken by the right-eye and left-eye image sensors 22 and 26 are fed via the driver 16 to the controller 4. The right-eye and left-eye deflecting zoom lens optical systems 24 and 28 have a zooming capability, whereby not only a real-scale (unity) image but also an enlarged image of the actual visual field and a consolidated image of a wide region of the actual visual field can be imaged on the right-eye and left-eye image sensors 22 and 26. The former is suitable for observation on an enlarged scale, and the latter is suitable to provide within the visual field a visual-field image that is wider than what is actually seen for a user with visual field constriction.

The imaging optical system employing the right-eye and left-eye deflecting zoom lens optical systems 24 and 28 described above helps reduce thickness in the incident optical axis direction, preventing the body 2a from protruding frontward excessively. Moreover, the right-eye and left-eye deflecting zoom lens optical systems 24 and 28 are configured such that the parts of the optical systems after deflection occupy spaces in the directions perpendicular to the lines of sight 6a and 8a respectively, and that the right-eye and left-eye image sensors 22 and 26 are arranged further inward in the direction of deflection. This arrangement helps avoid arranging components that shield outside the lines of sight 6a and 8a, so that the actual visual field outside the lines of sight 6a and 8a can be seen directly. While the human eyes are believed to be able to perceive information within a visual field as wide as about 200 degrees, the information of the visual field displayed on the right-eye and left-eye displays 12 and 14 in Example 1 covers about 40 degrees. Thus, Example 1 is so configured that the visual field outside the information displayed on the right-eye and left-eye displays 12 and 14 can be seen directly to obtain visual information.

With the configuration described above, in the vision aid system of Example 1, the visual-field images taken by the right-eye and left-eye image sensors 22 and 26 are fed to the controller 4 for processing that suits a user's symptoms, and the processed images returned from the controller 4 are displayed on the right-eye and left-eye displays 12 and 14 in an observable fashion, so that better visual information is obtained than when the visual field is directly seen with the eyes. For example, a user with night blindness (impaired dark adaptation) can be presented with images processed at an increased gain with dark parts boosted by gamma correction. On the other hand, a user with light aversion (impaired light adaptation) can be presented with images processed with high-luminance parts compressed by gamma correction. For another example, for enhanced legibility of characters and the like, white-black reversed images can be presented. Moreover, the visual field around the image information displayed on the right-eye and left-eye displays 12 and 14 can be seen directly to obtain visual information. Incidentally, as will be described later, the degree of transparency of the directly observed images is controlled to match them with the displayed images.

As mentioned above, in Example 1 of the present invention, in a normal state, the optical axis of the right-eye eyepiece optical system 18 which directs the virtual image of the right-eye display 12 to the right eye 6 coincides with the incident optical axis of the right-eye deflecting zoom lens optical system 24. Likewise, the optical axis of the left-eye eyepiece optical system 20 which directs the virtual image of the left-eye display 14 to the left eye 8 coincides with the incident optical axis of the left-eye deflecting zoom lens optical system 28. As necessary, under the control of the driver 16, the optical axis of the right-eye or left-eye eyepiece optical system 18 or 20 can be translated to be displaced from the line of sight 6a or 8a. This makes it possible to cope with, for example, a user with a disorder in the foveal vision due to age-related macular degeneration or the like by shifting the line of sight so that the image taken by the right-eye or left-eye image sensor 22 or 26 can be seen in an unaffected part, that is, elsewhere than in a central part, of the retina.

Moreover, as described above, Example 1 of the present invention is so configured that the actual visual field outside the lines of sight 6a and 8a can be seen directly as the background. Moreover, in the optical path, indicated by an arrow 30, leading into the right eye from outward, a right-eye variable-transmittance ND filter 32 is provided. The right-eye variable-transmittance ND filter 32 comprises, for example, a liquid crystal shutter, and its transmittance is variable, under the control of the driver 16, between a maximum transmittance and a light intercepting state. Likewise, in the optical path, indicated by an arrow 34, leading into the left eye from outward, a left-eye variable-transmittance ND filter 36 is provided, and its transmittance is variable, under the control of the driver 16, between a maximum transmittance and a light intercepting state. Thus, the transmittances of the right-eye and left-eye variable-transmittance ND filters 32 and 36 can be changed independently of each other. Changing their transmittances serves not only to assist the pupil's ability to adapt to change of lightness in the ambience, but also to enhance the visibility of the display (the right-eye and left-eye displays 12 and 14) by changing transmittances according to change of lightness, and in addition to match the image on the display with the directly observed image as the background. Furthermore, when white-black reversed display is performed on the display, the right-eye and left-eye variable-transmittance ND filters 32 and 36 are brought into the light intercepting state so as not to interfere observation of a white-black reversed image.

As will be clear from FIG. 1, the above-described components of Example 1 are all housed inside the body 2a, and no part of the body 2a protrudes from the front face. Accordingly, when seen from a person facing the user wearing the HMD 2, the HMD 2 appears something like ordinary sunglasses, and this alleviates the sense of annoyance of being observed with a special device.

The driver 16 in the body 2a of the HMD 2 is connected to the controller 4 by parallel data communication and a power supply line 38 to allow mutual communication and supply of electric power from the controller 4 to the HMD 2. Moreover, to allow change of the image processing performed for the right-eye and left-eye displays 12 and 14, an ambient light sensor 40 is provided in the temples 2b of the HMD 2, and information on the ambient light is fed to the controller 4 across a communication line 42. Furthermore, to alleviate abrupt image change as occurs when the user changes the direction of the face, in particular with an enlarged image, an acceleration sensor 44 is provided in the temples 2b, and information on the movement and the like of the face is fed to the controller 4 across a communication line 46. The parallel communication, the power supply line 38, and the communication lines 42 and 46 are in practice integrated into a single connection cable. Although FIG. 1 shows a configuration where the ambient light sensor 40 and the acceleration sensor 44 communicate directly with the controller, a configuration is also possible where communication is conducted via the driver 16 across parallel data communication and the power supply line 38.

The controller 4 has an interface 48 for communication with the HMD 2 and for supply of electric power to the HMD 2 as described above. An image processor 50 in the controller 4 processes images received via the driver 16 across parallel data communication and the power supply line 38 from the right-eye and left-eye image sensors 22 and 26 of the HMD 2, and feeds the result, as image data suitable to assist the user, to a display controller 52. From the display controller 52, the image data is transmitted across the parallel data communication and the power supply line 38 so that, based on the received image data, the driver 16 drives the right-eye and left-eye displays 12 and 14 to display images. Moreover, a background controller 54 controls the right-eye and left-eye variable-transmittance ND filters 32 and 36 across the parallel data communication and the power supply line 38.

A preset memory 56 stores preset values for image processing information and transmittance information (information on the transmittances of the right-eye and left-eye variable-transmittance ND filters 32 and 36) that suit the user's specific symptoms and the ambient light. An operation panel 58, in coordination with display on a controller display 60, accepts operations for entering preset values as mentioned above and operations for selecting image processing such as white-black reversal. A central controller 62 controls the image processor 50 according to the image processing information in the preset memory 56 as well as operations on the operation panel 58 and information from the ambient light sensor 40 and the acceleration sensor 44. The central controller 62 also controls a background controller 54 according to the transmittance information in the preset memory 56 as well as information from the ambient light sensor 40. Control data for the background controller 54 is transmitted across parallel data communication and the power supply line 38, and based on the received data, the driver 16 varies the transmittances of the right-eye and left-eye variable-transmittance ND filters 32 and 36 to control the lightness of the directly observed background. The central controller 62 further controls the display controller 52 and the controller display 60 in connection with the functions mentioned above. A power supply 64 supplies electric power to the entire controller 4 and also, via the interface 48, to the HMD 2.

Figure 2:
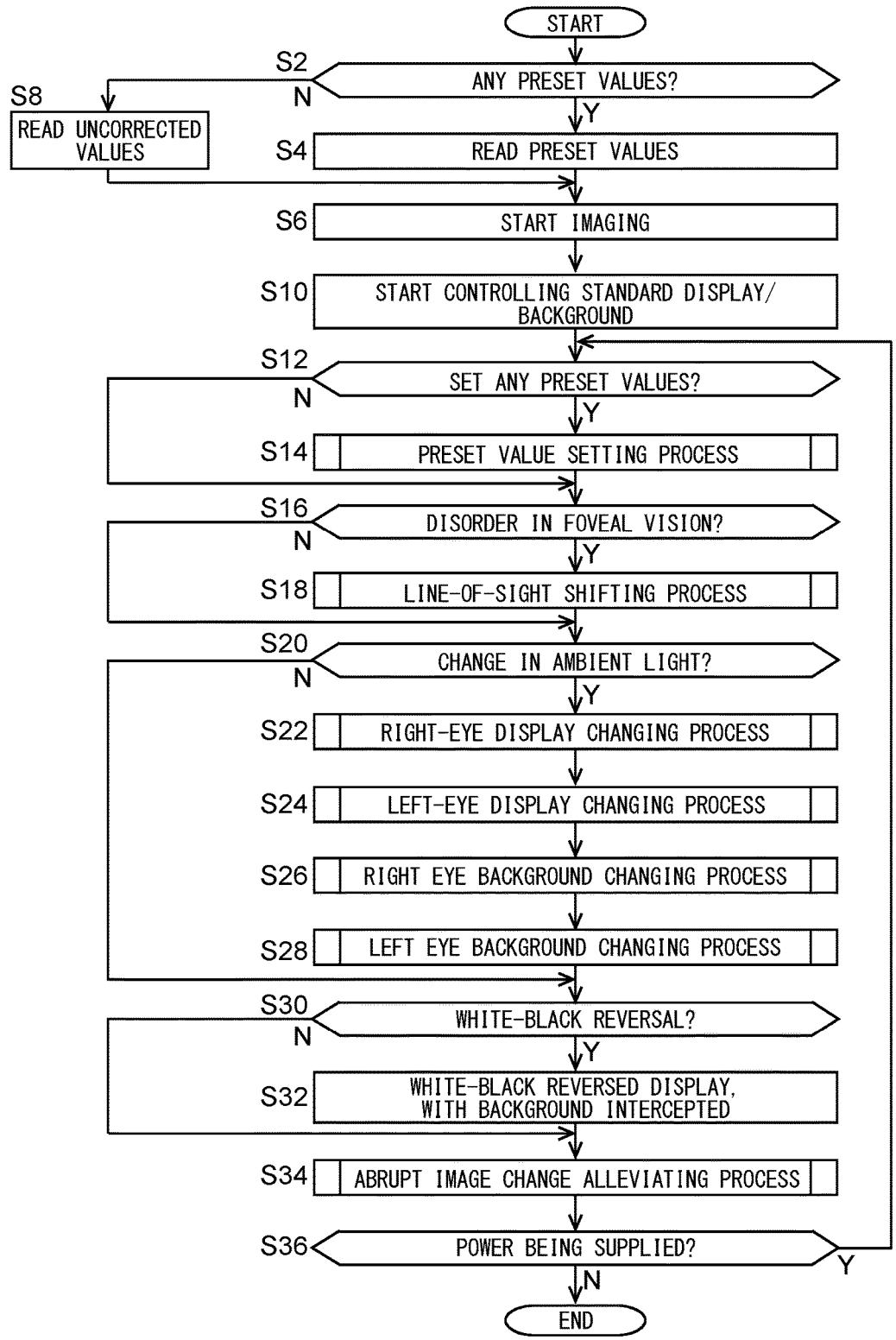
FIG. 2 is a basic flow chart explaining the operation of the central controller in Example 1.

FIG. 2 is a basic flow chart explaining the operation of the central controller 62 in Example 1. The flow starts when electric power starts to be supplied to the system. At Step S2, whether or not any preset value is stored is checked. If any, the flow proceeds to step S4, where the preset values is read from the preset memory 56, and the flow then proceeds to step S6. On the other hand, if, at step S2, no preset value is stored, the flow proceeds to step S8, where default values specifying no correction in image processing are read, and the flow then proceeds to step S6.

At step S6, imaging by the right-eye and left-eye image sensors 22 and 26 is started. The flow then proceeds to step S10, where display starts to be controlled in a standard state with predetermined lightness as a reference, and also the transmittances of the right-eye and left-eye variable-transmittance ND filters 32 and 36 start to be controlled to produce a background in a standard state that matches the display.

Subsequently, at step S12, whether or not an operation to set a preset value has been done is checked. If a setting operation is recognized to have been done, the flow proceeds to step S14, where a preset value setting process is performed, and the flow then proceeds to step S16. On the other hand, if, at step S12, no operation to set a preset value is recognized, the flow proceeds directly to step S16. The preset value setting process at step S14 will be described in detail later.

At step S16, whether or not a preset value indicating that the user has a disorder in the foveal vision is stored is checked, and if so, the flow proceeds to step S18, where a light-of-sight shifting process is performed, and the flow then proceeds to step S20. On the other hand, if, at step S16, the user is recognized not to have a disorder in the foveal vision, the flow proceeds directly to step S20. This establishes a normal state where, as described above, the optical axes of the right-eye and left-eye eyepiece optical systems 18 and 20 coincide with the incident optical axes of the right-eye and left-eye deflecting zoom lens optical systems 24 and 26 respectively.

At step S20, whether or not there has been a change in the lightness of the ambient light is checked, and if so, a right-eye display changing process at step S22 and a left-eye display changing process at step S24 are performed successively, and the flow proceeds to step S26. In this way, the right-eye and left-eye display changing processes are performed independently of each other. At step S26, a right-eye background changing process is performed, and subsequently, at step S28, a left-eye background changing process is performed. The flow then proceeds to step S30. In this way, the right-eye and left-eye background changing processes too are performed independently of each other. On the other hand, if, at step S20, there has been no change in the lightness of the ambient light, the flow proceeds directly to step S30.

At step S30, whether or not an operation for white-black reversal has been done is checked, and if so, the flow proceeds to step S32, where white-black reversed display is performed while the background is brought into a light-intercepting state so as not to interfere with the observation of the white-black reversed display, and the flow then proceeds to step S34. On the other hand, if, at step S30, no operation for white-black reversal is recognized, the flow proceeds directly to step S34. At step S34, an abrupt image change alleviating process (described in detail later) is performed. Then, at step S36, whether or not electric power is being supplied is checked and, if so, the flow returns to step S12 so that thereafter, so long as electric power is recognized to be being supplied, steps S12 through S36 are repeated. On the other hand, if, at step S36, electric power is not recognized to be being supplied, the flow ends immediately.

Figure 3:
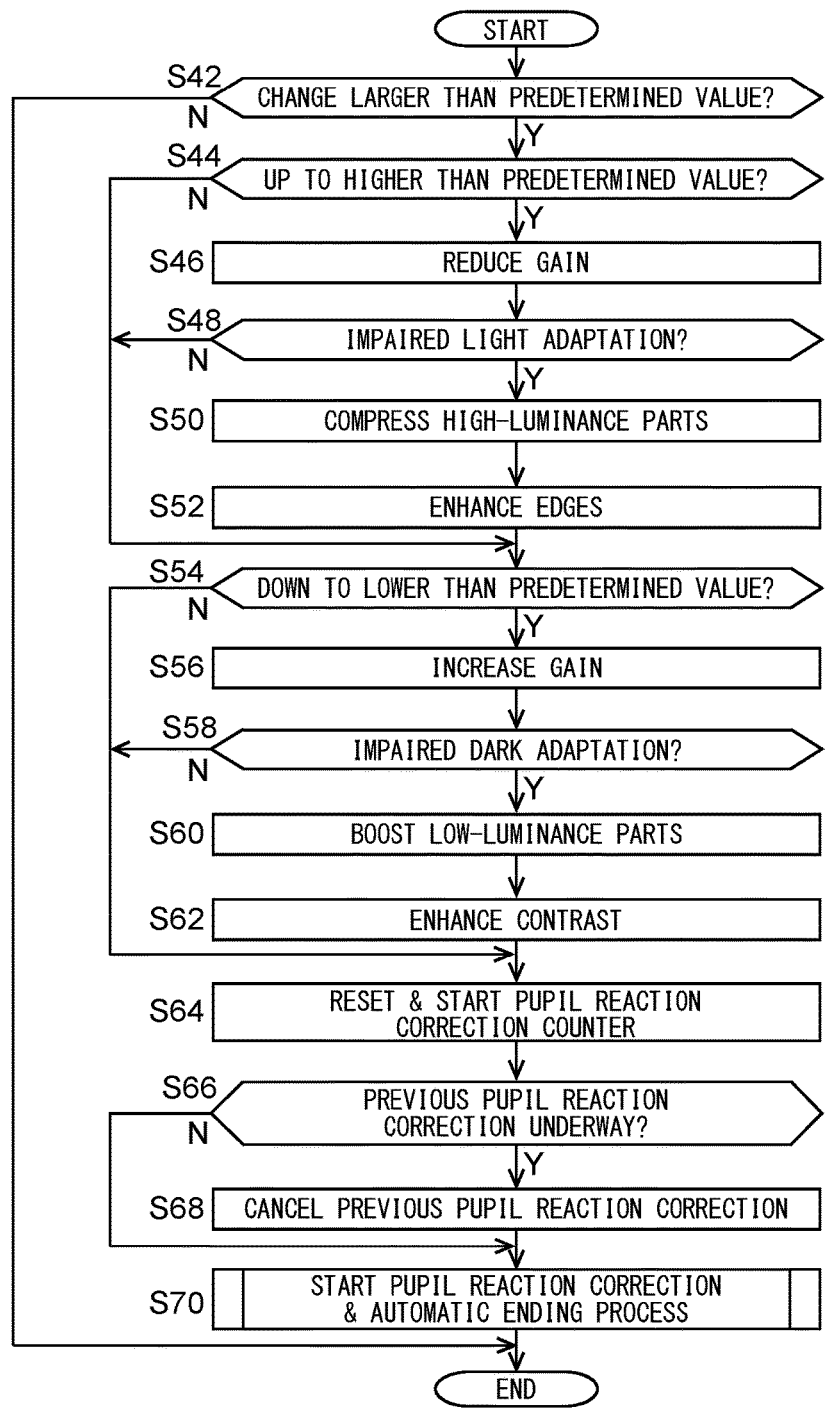
FIG. 3 is a flow chart showing the details of steps S22 and S24 in FIG. 2.

FIG. 3 is a flow chart showing the details of the right-eye display changing process at step S22 and the left-eye display changing process at step S24. What is done is common to those two steps, but is performed separately for the right and left eyes as shown in FIG. 2. At the start, the flow proceeds to step S42, where it is checked whether or not the change in the ambient light detected at step S20 in FIG. 2 is equal to or larger than a predetermined value set beforehand for the display changing process. If the change is equal to or smaller than the predetermined value and does not require the display changing process, the flow ends immediately, and a jump is made back to step S26 in FIG. 2.

On the other hand, if, at step S42, a change larger than the predetermined value is detected, the flow proceeds to step S44, where whether or not the change has caused the ambient light to be higher than a predetermined value is checked. If, at step S44, the ambient light is detected having become higher than the predetermined value, then at step S46, the gain of the image sensors 22 and 26 is reduced, and the flow proceeds to step S48. At step S48, whether or not the user has impaired light adaptation is checked, and if so, the flow proceeds to step S50, where gamma correction is performed to compress high-luminance parts, and the flow then proceeds to step S52. At step S52, edge enhancement is further performed, and the flow proceeds to step S54. On the other hand, if, at step S44, the ambient light is not detected having become higher than the predetermined value, or if, at step S48, the user is not confirmed to have impaired light adaptation, the flow proceeds directly to step S54.

At step S54, whether or not the change has caused the ambient light to be lower than the predetermined value is checked. If the ambient light is detected having become lower than the predetermined value, then at step S56, the gain of the image sensors 22 and 26 is increased, and the flow proceeds to step S58. At step S58, whether or not the user has impaired dark adaptation is checked, and if so, the flow proceeds to step S60, where gamma correction is performed to boost low-luminance parts, and the flow then proceeds to step S62. At step S62, contrast enhancement is further performed, and the flow proceeds to step S64. On the other hand, if, at step S54, the ambient light is not detected having become lower than the predetermined value, or if, at step S58, the user is not confirmed to have impaired dark adaptation, the flow proceeds directly to step S64.

At step S64, a counter for performing display change correction according to the time required by the pupil to adapt to a change in lightness is reset and started, and the flow proceeds to step S66. At step S66, it is checked whether or not pupil reaction correction based on the previous change in lightness is underway, and if so, the flow proceeds to step S68, where the previous pupil reaction correction is canceled, and the flow then proceeds to step S70. On the other hand, if, at step S66, no previous pupil reaction correction is detected being underway, the flow proceeds directly to step S70. At step S70, pupil reaction correction is started and in addition a process for automatically ending the pupil reaction correction at the end of a pupil reaction based on the counter is started, and the flow then ends.

Figure 4:
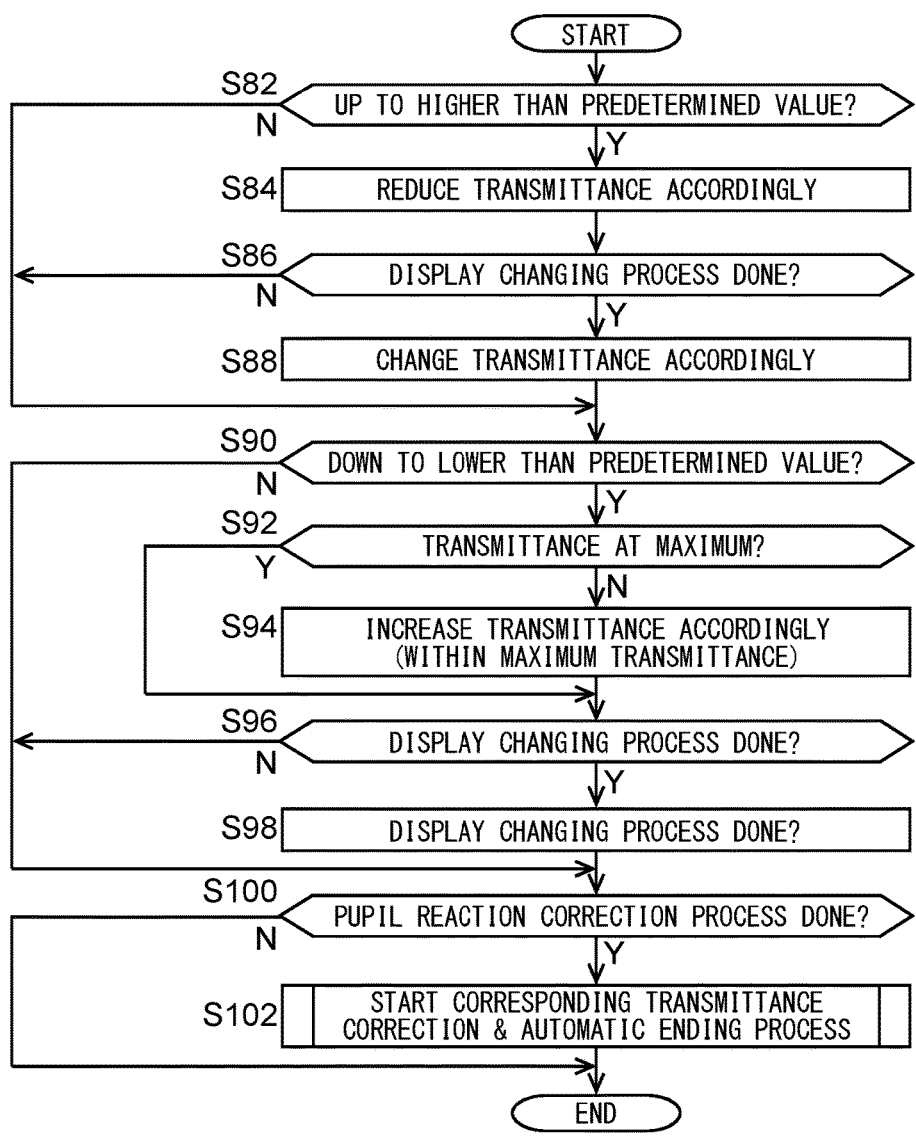
FIG. 4 is a flow chart showing the details of steps S26 and S28 in FIG. 2.

FIG. 4 is a flow chart showing the details of the right-eye and left-eye background changing processes at steps S26 and S28 in FIG. 2. What is done is common to those two steps, but is performed separately for the right and left eyes as shown in FIG. 2. At the start, the flow proceeds to step S82, where it is checked whether or not the change in the ambient light detected at step S20 in FIG. 1 has caused the ambient light to be higher than a predetermined value. Typically, the predetermined value at step S82 in FIG. 4 has a lower level than the predetermined value at step S44 in FIG. 3.

If, at step S82, the ambient light is detected having become higher than the predetermined value, the flow proceeds to step S84, where the transmittances of the right-eye and left-eye variable-transmittance ND filters 32 and 36 are reduced according to the increase in the ambient light, and the flow proceeds to step S86. At step S86, it is checked whether or not a display changing process has been performed based on the latest change in the ambient light, and if so, the flow proceeds to step S88, where the transmittances of the right-eye and left-eye variable-transmittance ND filters 32 and 36 are changed according to the display change, and the flow then proceeds to step S90. If, at step S82, the ambient light is not detected having become higher than the predetermined value, or if, at step S86, no display changing process is detected having been performed, the flow proceeds directly to step S90.

At step S90, it is checked whether or not the change in the ambient light detected at step S20 in FIG. 1 has caused the ambient light to be lower than a predetermined value. Typically, the predetermined value at step S90 in FIG. 4 has a higher level than the predetermined value at step S54 in FIG. 3. If, at step S90, the ambient light is detected having become lower than the predetermined value, the flow proceeds to step S92, where whether or not the transmittances of the right-eye and left-eye variable-transmittance ND filters 32 and 36 are already at their maximum. If not, the flow proceeds to S94, where the transmittances of the right-eye and left-eye variable-transmittance ND filters 32 and 36 are increased according to the increase in the ambient light, and the flow then proceeds to step S96. The increase here, however, does not exceed the maximum transmittance. On the other hand, if, at step S92, the transmittances of the right-eye and left-eye variable-transmittance ND filters 32 and 36 are already at their maximum, the flow proceeds directly to step S96.

At step S96, it is checked whether or not a display changing process has been performed based on the latest change in the ambient light, and if so, the flow proceeds to step S98, where the transmittances of the right-eye and left-eye variable-transmittance ND filters 32 and 36 are changed according to the display change, and the flow then proceeds to step S100. The increase here, however, does not exceed the maximum transmittance. On the other hand if, at step S90, the ambient light is not detected having become lower than the predetermined value, or if, at step S96, no display changing process is detected having been performed, the flow proceeds directly to step S100.

At step S100, it is checked whether or not any pupil reaction correction process that was started for display change in FIG. 3 is underway, and if so, the flow proceeds to step S102, where corresponding correction of the transmittances of the right-eye and left-eye variable-transmittance ND filters 32 and 36 is started and in addition a process for automatically ending the correction according to the pupil reaction correction for display change is started, and the flow then ends.

Figure 5:
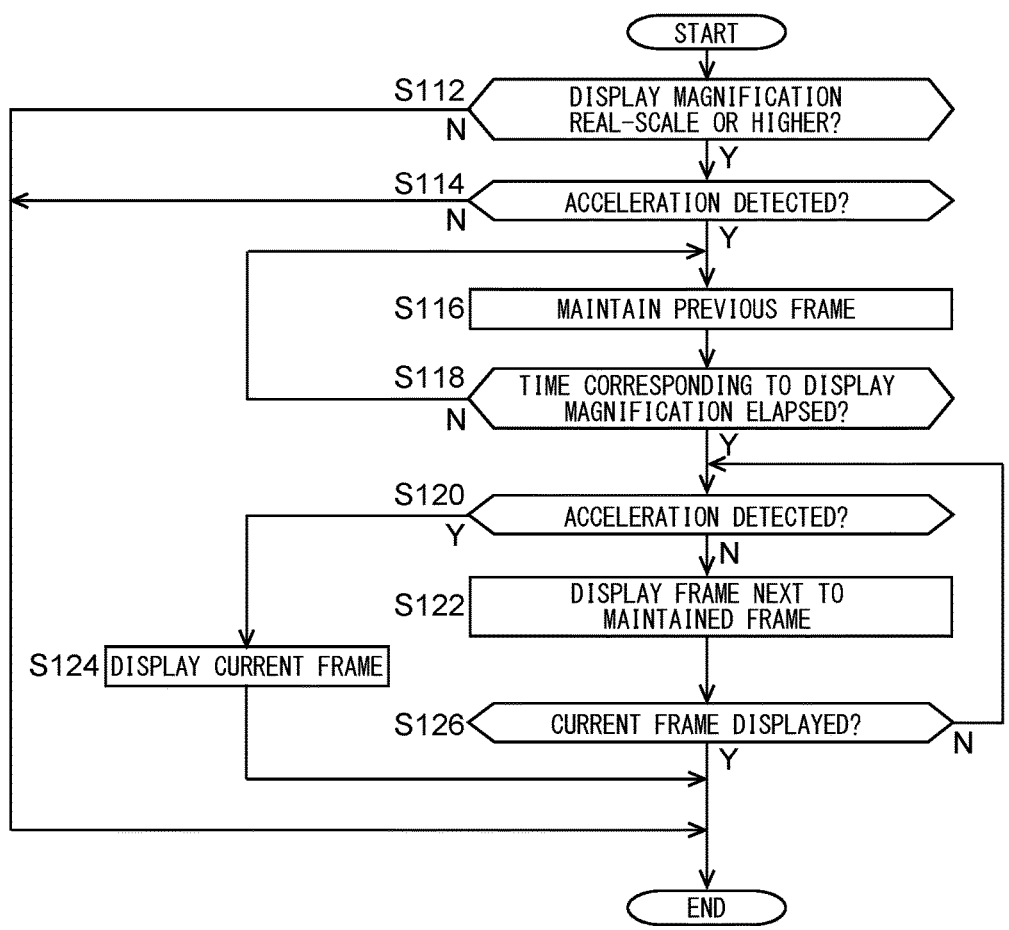
FIG. 5 is a flow chart showing the details of step S34 in FIG. 2.

FIG. 5 is a flow chart showing the details of the abrupt image change alleviating process at step S34 in FIG. 2. When the flow starts, at step S112, whether or not the display magnification is real-scale (unity) or higher is checked. If not, that is, if the display magnification is equal to or lower than the magnification of the background and thus no alleviation of abrupt image change is needed even when, for example, the direction of the face is changed, the flow ends immediately, and a jump is made to step S36 in FIG. 2.

By contrast, if, at step S112, the display magnification is detected being real-scale or higher, the flow proceeds to step S114, where it is checked whether or not acceleration resulting from the direction of the face being changed is detected. If acceleration is detected, the flow proceeds to step S116, where the display of the previous frame on the right-eye and left-eye displays 12 and 14 is maintained, and the flow proceeds to step S118. At step S118, it is checked whether or not a time set beforehand according to the display magnification (for example, a time corresponding to three frames for a display magnification of 2 times) has elapsed. If not, the flow returns to step S116, and thereafter, until the time is detected to have elapsed, steps S116 and S118 are repeated to maintain the previous frame. On the other hand, if, at step S118, the time is detected to have elapsed, the flow proceeds to step S120.

At step S120, the check for acceleration is done once again so that, if no acceleration is detected any longer as a result of the face ceasing to move, the flow proceeds to step S122, where the frame next to the one maintained at step S116 is displayed, and the flow then proceeds to step S126. The display of the next frame at step S112 is performed at a higher frame rate than normally is. At step S126, it is checked whether or not the display has caught up with the current frame. If not, the flow returns to step S120. Thereafter, unless acceleration is detected anew at step S120 and in addition the current frame is caught up with at step S126, steps S120 through S126 are repeated, so that a return to the current frame is made at a frame rate higher than the normal frame rate. When, at step S126, the current frame is detected being displayed, the flow ends. In this way, abrupt image change occurring when the direction of the face is changed at a high magnification is alleviated, and the motion of the image is delayed. This delay is canceled quickly when the face ceases to move. On the other hand, if, at step S120, acceleration is detected and the face keeps moving, the flow proceeds to step S124, where the current frame is displayed, and the flow then ends. In this way, while the face keeps moving, abrupt image change is alleviated through sporadic skipping of frames.

Figure 6:
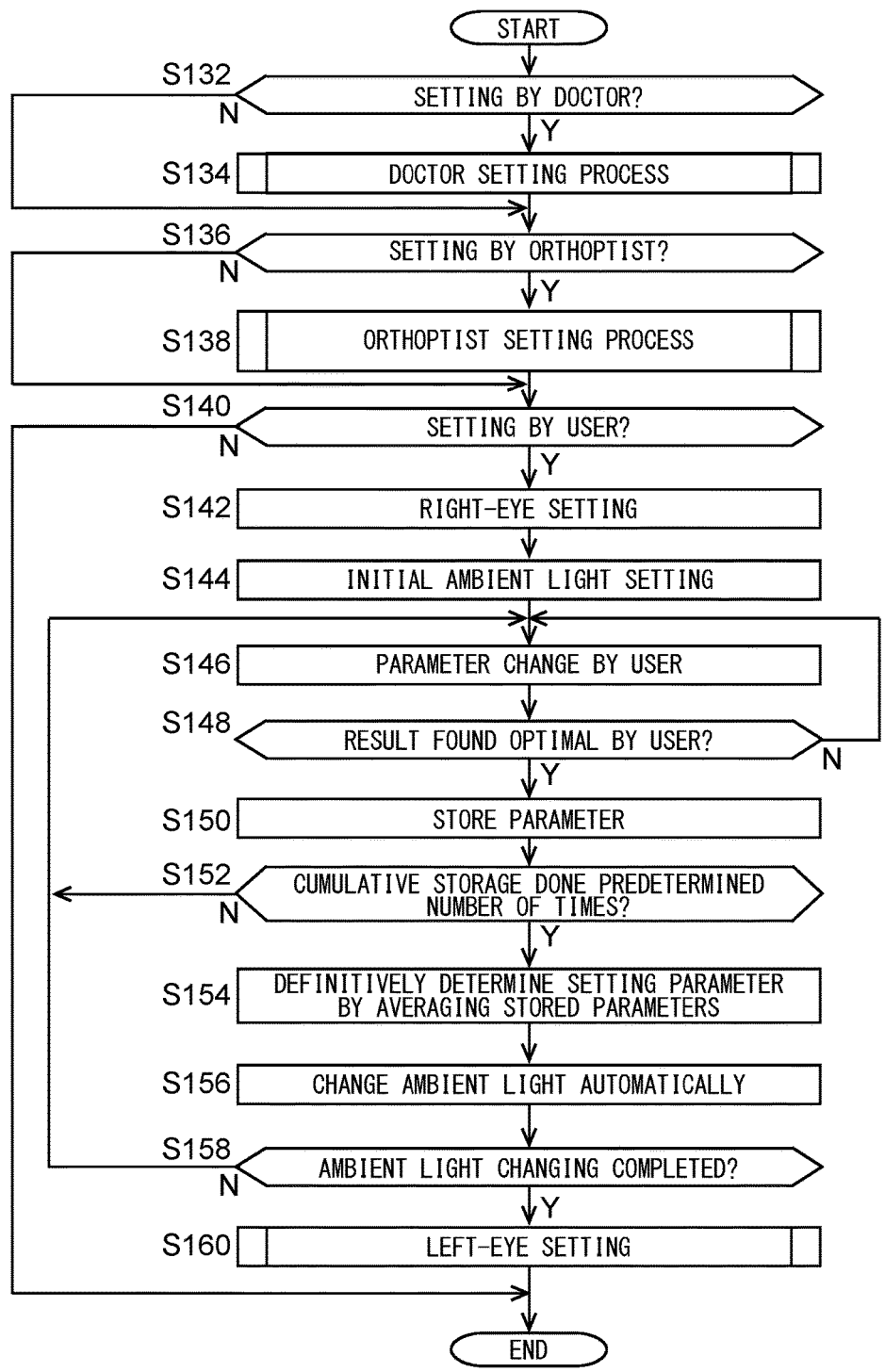
FIG. 6 is a flow chart showing the details of step S14 in FIG. 2.

FIG. 6 is a flow chart showing the details of the preset value setting process at step S14 in FIG. 2. When the flow starts, at step S132, whether or not the setter is a medical doctor is checked. If so, the flow proceeds to step S134, where a doctor setting process is performed, and the flow then proceeds to step S136. On the other hand, if, at step S132, the setter is not recognized to be a doctor, the flow proceeds directly to step S136. At step S136, whether or not the setter is an orthoptist is checked. If so, the flow proceeds to step S138, where an orthoptist setting processing is performed, and the flow then proceeds to step S149. On the other hand, if, at step S136, the setter is not recognized to be an orthoptist, the flow proceeds directly to step S140.

At step S140, whether or not the setter is the user himself is checked. If so, at step S142, right-eye setting is started and, at step S144, initial ambient light setting is performed. During setting by a user, the user himself actually wears the HMD 2 and sees the right-eye display 12 to check whether or not a setting is proper. Specifically, at step S146, a display correction parameter is changed by the user himself. Then, at step S148, the user is prompted to judge whether or not the image observed on the right-eye display 12 is optimal. If the user does not find it optimal, the flow returns to step S146, and thereafter steps S146 and S148 are repeated to permit the user to change the parameter and judge the result repeatedly. Then if, at step S148, the user finds what he observes optimal and operates the operation panel 58 accordingly, the flow proceeds to step S150, where the parameter in that state is stored. The flow then proceeds to step S152.

At step S152, it is checked whether or not cumulative storage of parameters, which are stored as described above, has been performed a predetermined number of times. If, at step S152, cumulative storage has not been performed the predetermined number of times yet, the flow returns to step S146, where steps S146 through S152 are repeated until cumulative storage is performed the predetermined number of times. On the other hand, if, at step S152, cumulative storage has been performed the predetermined number of times, the flow proceeds to step S154, where the stored parameters are averaged and setting parameters are determined definitively.

Subsequently, at step S156, the ambient light is changed automatically for the purpose of setting, and the flow then proceeds to step S158. At step S158, whether or not the ambient light changing process has been completed is checked. If the changing process has not been completed, the flow returns to step S146, and thereafter, so long as ambient light changing is not completed, steps S146 through S158 are repeated, so that right eye setting is continued. On the other hand, if, at step S158, the ambient light changing process is completed, the flow proceeds to a left-eye setting process at step S160. The details of the left-eye setting process at step S160 are the same as those of the right-eye setting process, and for simplicity's sake, the whole process is illustrated in an integrated fashion at step S160. When the left-eye setting process at step S160 is completed, the flow ends, and a jump is made back to step S16 in FIG. 2. On the other hand, if, at step S140, the setter is not detected being the user himself, the flow ends immediately.

The various features of Example 1 described above can be implemented not only in Example 1 described above but also, so long as they provide their benefits, in any other examples. For example, although the flow in FIG. 3 deals with a configuration where, for a user with impaired light adaptation, edge enhancement is performed and, for a user with impaired dark adaptation, contrast enhancement is performed, what process to perform in what case is arbitrary: edge enhancement and contrast enhancement may both be adopted irrespective of whether the user has impaired light adaptation or impaired dark adaptation.

EXAMPLE 2

Figure 7:
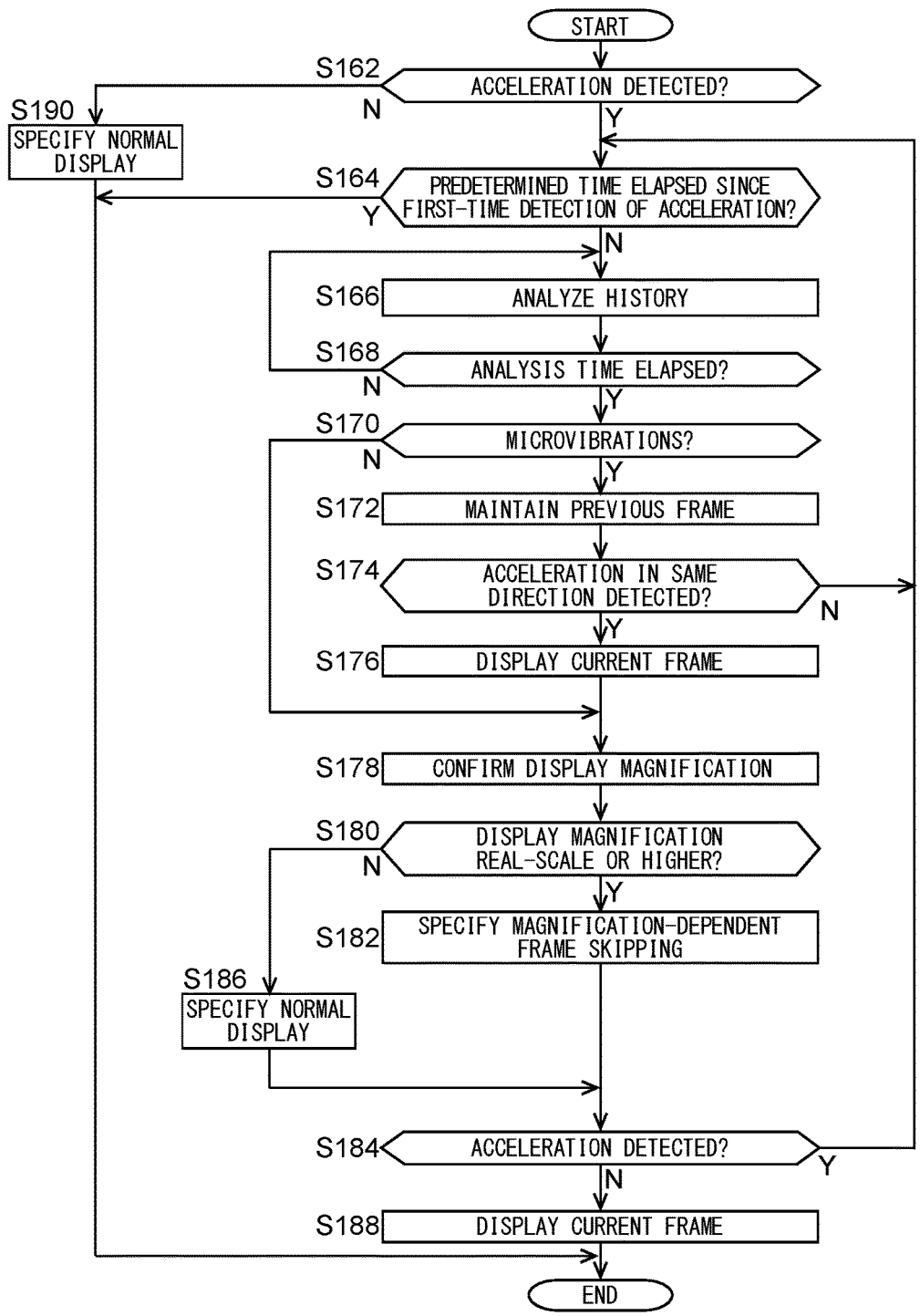
FIG. 7 is a flow chart showing the details of the abrupt image change alleviating process in a vision aid system in Example 2 embodying the present invention (Example 2)

FIG. 7 is a flow chart showing the details of the abrupt image change alleviating process in a vision aid system in Example 2 embodying the present invention. Example 2 shares the same overall configuration as that of Example 1 shown in the block diagram in FIG. 1, and shares the same basic operation as that of Example 1 shown in the basic flow chart in FIG. 2. Accordingly, for common features, Example 1 is to be referred to auxiliarily, and no overlapping description will be repeated. Example 2 differs from Example 1 in the specific configuration of the abrupt image change alleviating process at step S34 in FIG. 2. The flow chart in FIG. 7 thus shows the details of step S34 in FIG. 2, which is referred to auxiliarily in connection with Example 2.

When the flow in FIG. 7 starts, at step S162, whether or not acceleration equal to or more than a predetermined quantity is detected is checked. If such acceleration is detected, the flow proceeds to step S164, where it is checked whether or not a predetermined time (for example, two seconds) has elapsed since acceleration was detected for the first time in a sequence of acceleration detection events. If the predetermined time has not elapsed, the flow proceeds to step S166, where a historical analysis of the sequence of acceleration detection events is performed, and the flow then proceeds to step S168. At step S168, it is checked whether or not a predetermined time (for example, 0.5 seconds) has elapsed since the analysis was started. If the predetermined time has not elapsed, the flow returns to step S166, and thereafter, until the predetermined time elapses, steps S166 and S168 are repeated to continue the analysis.

On the other hand, if, at step S168, the predetermined time is recognized to have elapsed since the analysis was started, the flow proceeds to step S170, where it is checked whether or not the result of the historical analysis indicates that the detected sequence of changes in acceleration corresponds to minute vibrations. If minute vibrations are detected, the flow proceeds to step S172, where the display of the previous frame is maintained and the display is kept from being changed. This is to prevent image shake resulting from minute vibrations such as involuntary quivering of the body. Then, at step S174, whether or not acceleration in the same direction is detected is checked.

If, at step S174, no acceleration in the same direction is detected, the flow returns to step S164, and thereafter, so long as it is not recognized at step S164 that the predetermined time has elapsed since acceleration was detected for the first time, steps S164 through S174 are repeated. On the other hand, if, at step S174, acceleration in the same direction is detected, it is judged that the user made an intentional motion, as by changing the direction of the face, and the flow proceeds to step S176. At step S176, the display is changed from the change-inhibited state to the current frame, and the flow proceeds to step S178. Incidentally, if, at step S170, the historical analysis does not indicate minute vibrations, the flow proceeds to step S178 immediately.

At step S178, the current display magnification is checked, and the flow then proceeds to step S180, where whether or not the display magnification is real-scale (unity) or higher is checked. If it is real-scale or higher, then, at step S182, magnification-dependent frame skipping is specified, and the flow proceeds to step S184. In the magnification-dependent frame skipping at step S182, frame skipping that depends on the magnification is performed, as by reducing the frame rate to one-half when the magnification is 1.5 times and reducing the frame rate to one-third when the magnification is 2 times, so that, the higher the magnification, the lower the frame rate. This prevents subtle movements of the image in a short period, and thereby prevents motion sickness or the like due to an enlarged image. On the other hand, if, at step S180, the image is not real-scale or higher, the flow proceeds to step S186, where display at the normal frame rate is specified, and the flow proceeds to step S184.

At step S184, whether or not there is acceleration is detected once again, and if acceleration is still detected, the flow returns to step S164 so that thereafter, so long as it is not recognized at step S164 that the predetermined time has elapsed since acceleration was detected for the first time, steps S164 through S188 are repeated. On the other hand, if, at step S184, it is confirmed that no acceleration is detected, the flow proceeds to step S188, where display of the current frame is specified and the flow ends.

If, at step S164, it is detected that the predetermined time has elapsed since acceleration was detected for the first time, even if acceleration is still detected, the flow ends immediately. This is to prevent the other tasks in FIG. 2 from being kept unexecuted as a result of the flow in FIG. 7 being continued for a long time. As will be clear from FIG. 2, unless there is another task, the step S34 is reached in the course of repetition of steps S12 through S36; thus, the flow in FIG. 7 is repeated, and whenever acceleration is detected, the corresponding function in FIG. 7 can be continued. Incidentally, if, at step S162, no acceleration is detected, the flow proceeds to step S190, where display at the normal frame rate is specified and the flow ends. In this case, substantially none of the operations in the flow in FIG. 7 are performed; even so, step S190 is provided to cope with a case where step S162 is reached in other than a normal display state and no acceleration is detected.

EXAMPLE 3

Figure 8:
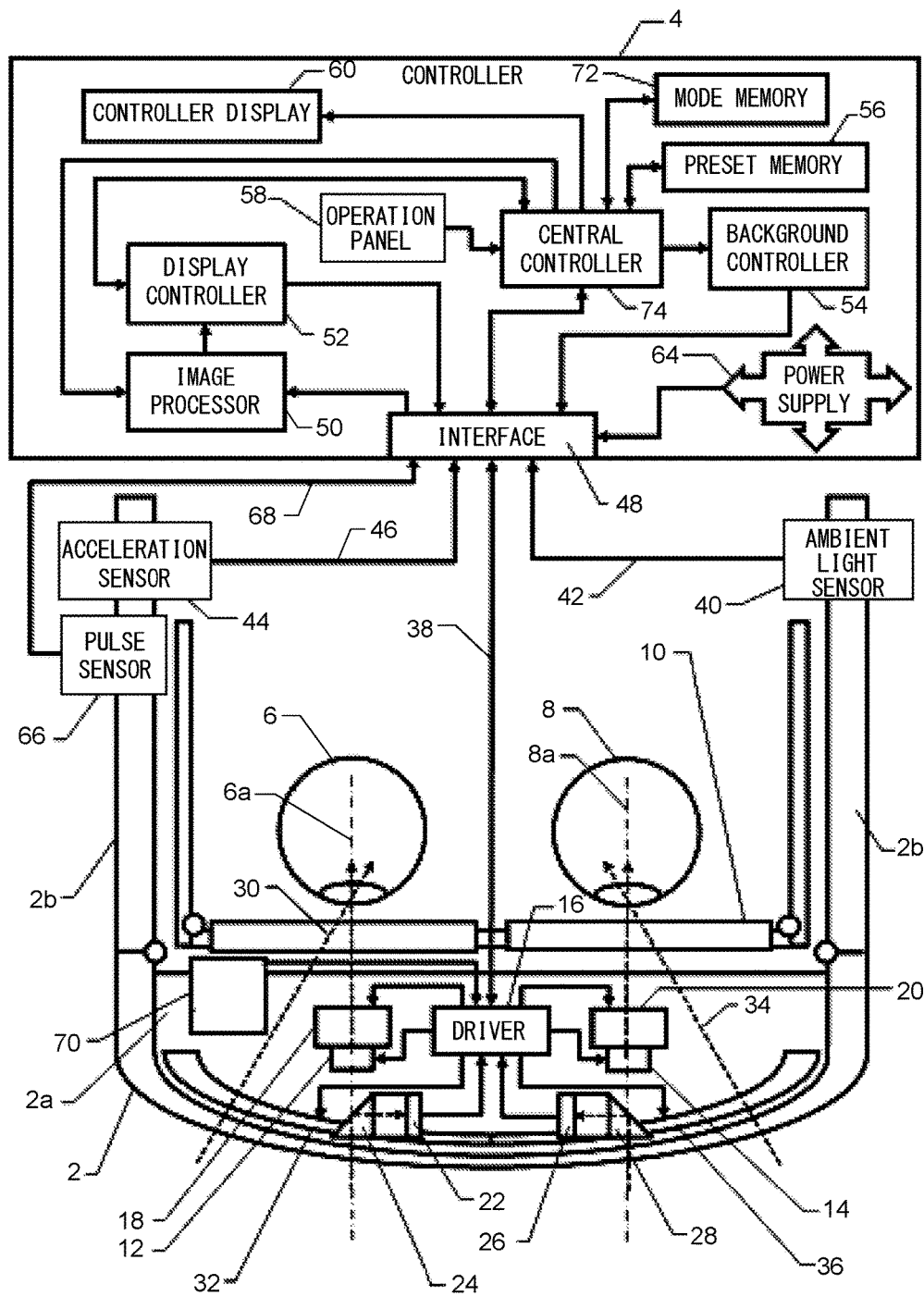
FIG. 8 is a block diagram showing the overall configuration of a vision aid system in Example 3 embodying the present invention (Example 3)

FIG. 8 is a block diagram showing the overall configuration of a vision aid system in Example 3 embodying the present invention. The configuration of Example 3 in FIG. 8 has much in common with Example 1 in FIG. 1; accordingly the same parts are identified by the same reference signs, and no overlapping description will be repeated. A first difference of Example 3 from Example 1 is that a pulse sensor 66 for detecting the pulse is provided in the temples 2*b* so that information as to whether the user is at rest or in action, as in the course of walking, is fed to the controller 4 across a communication line 68. As in Example 1, parallel data communication, the power supply line 38, and the communication lines 42, 46, and 68 are in practice integrated into a single connection cable. Again, although FIG. 8 shows a configuration where the ambient light sensor 40, the acceleration sensor 44, and the pulse sensor 66 communicate directly with the controller 4, a configuration is also possible where communication is conducted via the driver 16 across parallel data communication and the power supply line 38.

A second difference of the Example 3 shown in FIG. 8 from Example 1 in FIG. 1 is that a line-of-sight sensor 70 is provided in the HMD 2 to detect the movement of the user's line of sight. Information on the movement of the user's line of sight and the like as detected by the line-of-sight sensor 70 is fed to the controller 4 via the driver 16 by parallel data communication. The pulse sensor 66 and the line-of-sight sensor 70 will be described in detail later. In Example 3, the ambient light sensor 40, the acceleration sensor 44, the pulse sensor 66, the line-of-sight sensor 70, and the like serve to detect the circumstances in which the HMD 2 is used, and are thus collectively referred to as circumstance sensors.

A third difference of Example 3 shown in FIG. 8 from Example 1 in FIG. 1 is that the controller 4 has a mode memory 72 in which different modes, such as an enlargement mode, a wide mode, and a white-black reversal mode, are registered in association with learned information. Learned information is registered for each mode through the learning, in that mode, of what the different circumstance sensors detect and how the operation panel 58 is operated. Based on the information registered in the mode memory 72, and in coordination with a central controller 74, restrictions are imposed on the selection of modes on the operation panel 58, and registered modes are selected automatically. The details will be given later.

Figure 9:
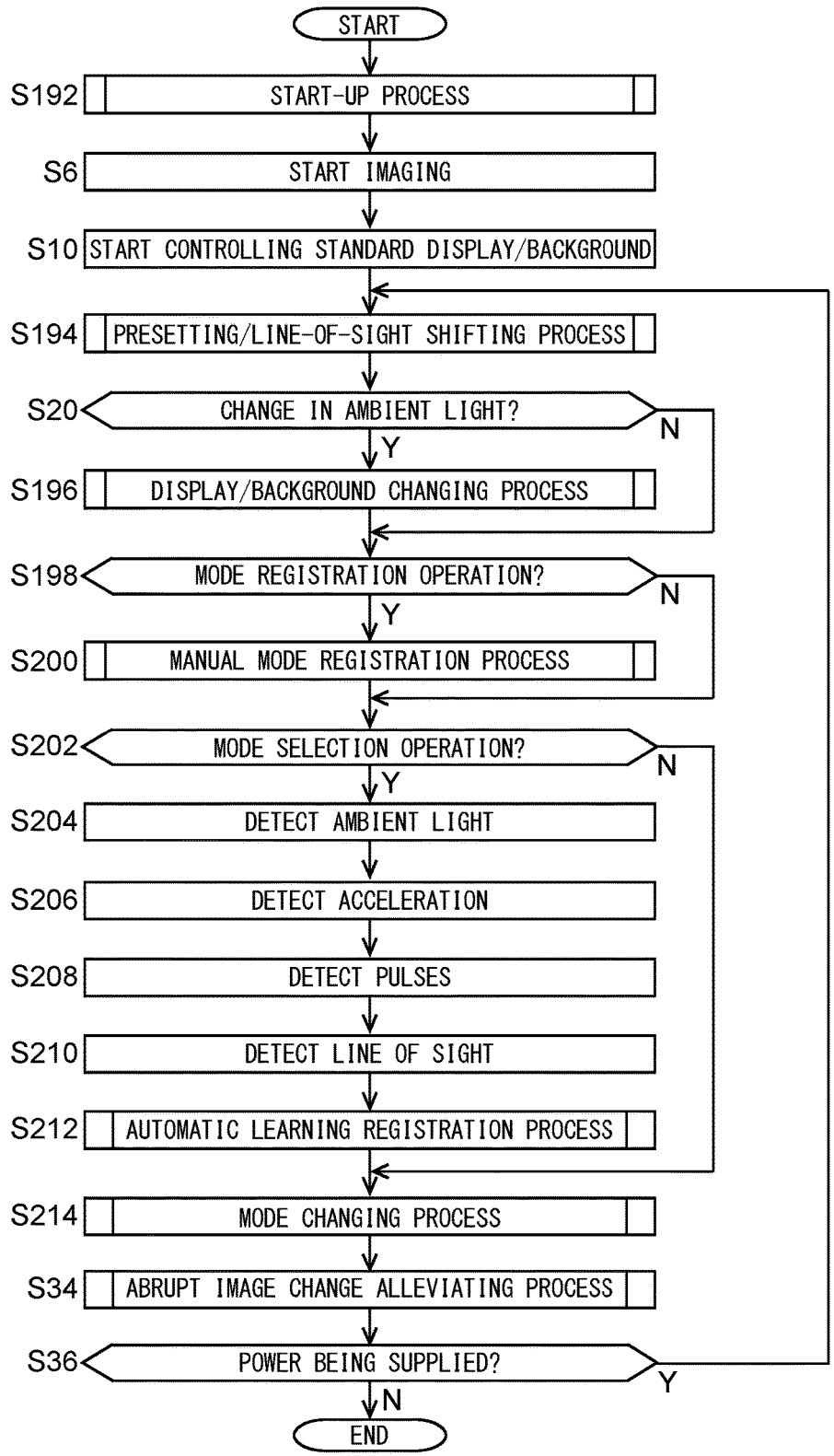
FIG. 9 is a basic flow chart explaining the operation of the central controller in Example 3.

FIG. 9 is a basic flow chart explaining the operation of the central controller 74 in Example 3. The flow in FIG. 9 has much in common with the flow in FIG. 2 in Example 1; accordingly, common steps are identified by common step numbers, and no overlapping description will be repeated; likewise, common groups of steps are illustrated in an integrated fashion, and no overlapping description will be repeated. Specifically, the start-up process at step S192 has steps S2, S4 and S8 in FIG. 2 integrated together; the presetting/line-of-sight shifting process at step S194 has steps S12 through S18 in FIG. 2 integrated together; and the display/background changing process at step S196 has steps S22 through S28 in FIG. 2 integrated together.

When step S198 is reached through the display/background changing process at step S196, it is checked whether or not a manual mode registration operation has been done to selectably register a mode other than a normal mode, such as an enlargement mode, a wide mode, or a white-black reversal mode. If a mode registration operation has been done, the flow proceeds to step S200, where a manual mode registration process according to the operation is performed, and the flow then proceeds to step S202. On the other hand, if, at step S198, no mode registration operation is detected, the flow proceeds directly to step S202.

At step S202, whether or not a manual operation to select a mode has been done is checked. If a mode selection operation has been done, the flow proceeds to step S204 and the following steps to detect the circumstances in which the operation was done. Specifically, at step S204, the ambient light is detected with the ambient light sensor 40; then at step S206, acceleration is detected with the acceleration sensor 44; and then at step S208, the pulse is detected with the pulse sensor 66. Moreover, at step S210, the movement of the line of sight is detected with the line-of-sight sensor 70.

Subsequently, at step S212, an automatic learning registration process is performed whereby what the different circumstance sensors detected when the mode was selected manually is learned and is automatically registered in that mode. In this process, for example, if an enlargement mode and a white-black reversal mode were selected in a still state free of acceleration and in addition in a resting state based on the pulse with only a limited movement of the line of sight detected, then it is learned that the enlargement mode and the white-black reversal mode are to be selected in such states, and those detected states are registered in the enlargement mode and the white-black reversal mode. That is, a registration is made on the assumption that, in such states, the user is interpreted to have selected the enlargement mode and the white-black reversal mode to read a book or viewing a document.

The information registered through the automatic mode learning process at step S212 is used in the cross-checking of properness of automatic selection of a general mode as will be described later, and also in automatic custom mode setting based on fulfilment of a learning result condition unique to a user. On completion of the automatic mode learning process at step S121, the flow proceeds to step S214. On the other hand, if, at step S202, no mode selection operation is detected, the flow proceeds directly to step S214. At step S214, a mode changing process is performed, which will be described in detail later. On completion of the mode changing process at step S214, the flow proceeds to step S34. Step S34 and the following steps are shared with FIG. 2.

Figure 10:
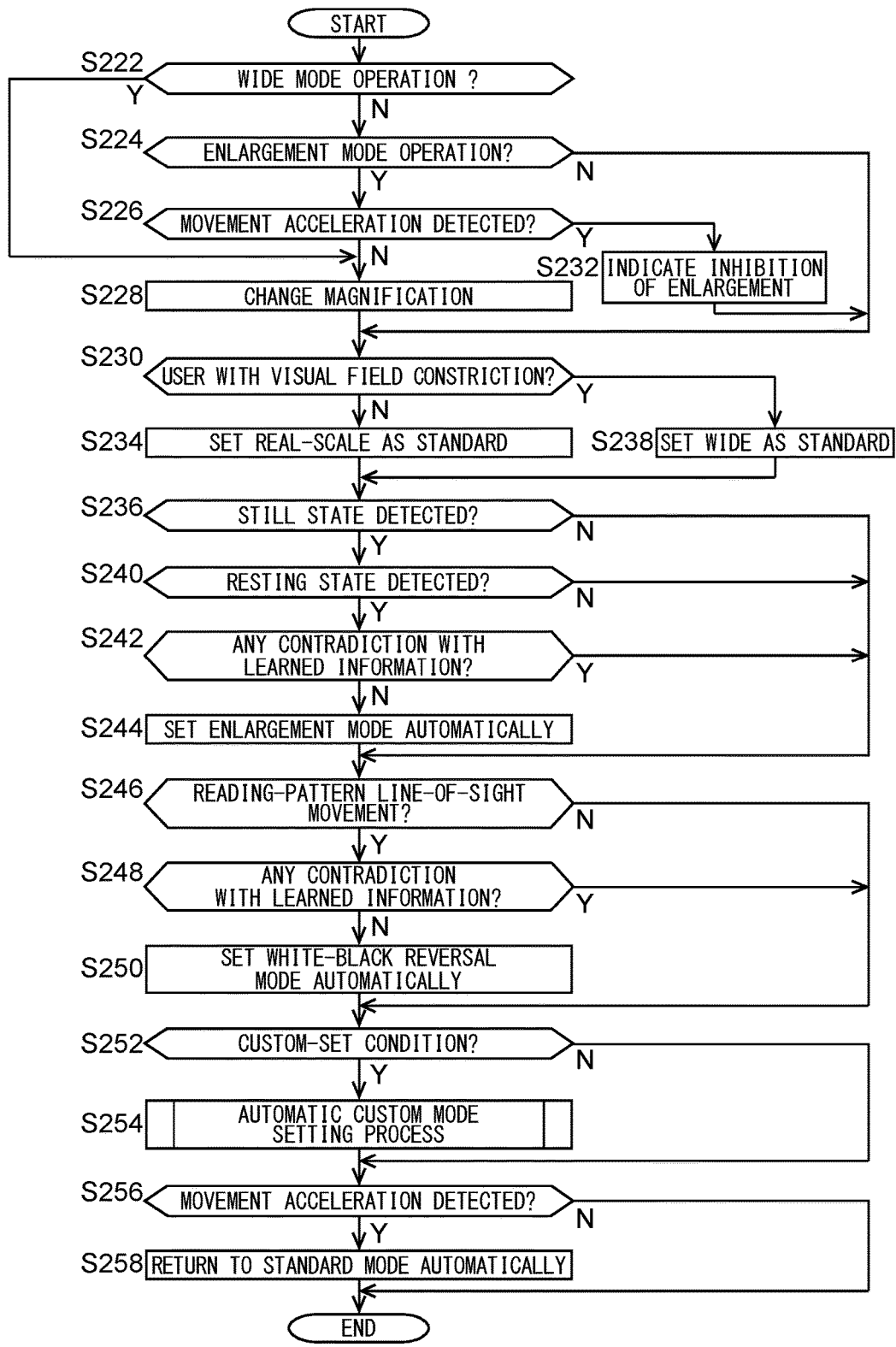
FIG. 10 is a flow chart showing the details of step S214 in FIG. 9.

FIG. 10 is a flow chart showing the details of the mode changing process at step S214 in FIG. 9. When the flow starts, at step S222, it is checked whether or not a manual operation to switch to a wide mode has been done. If no such operation is detected, the flow proceeds to step S224, where it is checked whether or not a manual operation to switch to an enlargement mode has been done. If a manual operation to switch to an enlargement mode is detected, the flow proceeds to step S226, where it is checked whether or not acceleration indicating that the user is moving is detected. If no acceleration is detected, the flow proceeds to step S228, where the magnification is changed as operated (in this case, to a magnification for the "enlargement mode"), and the flow then proceeds to step S230.

On the other hand, if, at step S226, acceleration indicating that the user is moving is detected, the flow proceeds to step S232, where an indication to the effect that enlargement is inhibited is displayed on the controller display 60, and the flow proceeds to step S230 without changing the magnification. The message to the effect that enlargement is not permitted may be displayed in a form superimposed on either of the images of the right-eye and left-eye image sensors 22 and 26.

On the other hand, if, at step S222, a manual operation to switch to a wide mode is detected having been done, the flow proceeds directly to step S228, where the magnification is changed as operated (in this case, to a magnification for the "wide mode"), and the flow proceeds to step S230. In this way, an operation to reduce the magnification does not pose a great danger even to a user who is moving, and accordingly the operation is performed immediately without checking for acceleration. Incidentally, if, at step S224, no enlargement mode operation is detected, this means that no manual operation to change the magnification has been done, and thus the flow proceeds to step S23 immediately.

At step S230, whether or not the user has visual field constriction is checked. If the user does not have visual field constriction, the flow proceeds to step S234, where real-scale display is set as a standard mode, and the flow then proceeds to step S236. On the other hand, if, at step S230, the user is recognized to have visual field constriction, the flow proceeds to step S238, where wide display is set as a standard mode, and the flow proceeds to step S236.

Step S236 and the following steps relate to automatic mode change. First, at step S236, based on the acceleration sensor 44, whether or not the user is in a still state is checked. If the user is in a still state, the flow proceeds to step S240, where, based on the pulse sensor 66, whether or not the user in in a resting state is checked. If the user is in the resting state, the flow proceeds to step S242, where it is checked whether or not automatically switching to the enlargement mode in such states contradicts the user's manual setting behavior thus far. If no contradiction is recognized, then, at step S244, the enlargement mode is automatically set, and the flow proceeds to step S246. On the other hand, if, at step S236, no still state is detected, or if, at step S240, no resting state is detected, or if, at step S242, contradiction with learned information is detected, the flow proceeds to step S246 without automatically setting the enlargement mode. Here, contradiction with learned information is recognized in such cases as where, despite a still state and in addition a resting state being detected in the automatic registration process from step S202 through S212 in FIG. 9, there is scarce history of the enlargement mode having been selected manually, or where there is a history of the enlargement mode, once automatically set based on a still state and in addition a resting state, having been cancelled manually. In such cases, even if a still state and a resting state are detected, it is highly likely that automatically setting the enlargement mode will be contrary to the user's intention, and therefore the flow proceeds to step S246 without automatically setting the enlargement mode.

At step S246, the movement of the user's line of sight based on the output of the line-of-sight sensor 70 is compared with reference data indicating reading-pattern line-of-sight movement, and it is checked whether or not the movement of the user's line of sight corresponds to the reading-pattern line-of-sight movement. If it is recognized as the reading-pattern line-of-sight movement, the flow proceeds to step S248, where it is checked whether or not automatically switching to the white-black reversal mode when reading-pattern movement is detected does not contradict the user's manual setting behavior thus far. If no contradiction is recognized, then, at step S250, the white-black reversal mode is automatically set, and the flow proceeds to step S252. On the other hand, if, at step S246, no reading-pattern line-of-sight movement is detected, or if, at step S248, contradiction with learned information is detected, the flow proceeds to step S252 without automatically setting the white-black reversal mode. Here, contradiction with learned information is recognized, as described above in connection with step S242, in cases such as where, despite reading-pattern line-of-sight movement being detected in the automatic registration process from step S202 through S212 in FIG. 9, there is scarce history of the white-black reversal mode having been selected manually, or where there is a history of the white-black reversal mode, once automatically set based on reading-pattern line-of-sight movement, having been cancelled manually. In such cases, even if reading-pattern line-of-sight movement is detected, it is highly likely that automatically switching to the white-black reversal mode will be contrary to the user's intention, and accordingly the flow proceeds to step S252 without automatically switching to the white-black reversal mode.

In the automatic setting from step S236 through S250, if the automatic setting of the enlargement mode at step S244 is gone through and then the automatic setting of the white-black reversal mode at step S250 is performed, enlarged display is white-black reversed. On the other hand, if the automatic setting of the enlargement mode at step S244 is performed but no reading-pattern line-of-sight movement is detected at step S246, the user may be, for example, sitting on a stool and performing assembly work or the like, and thus white-black reversal, which is suitable for the reading of characters, is often unsuitable. Accordingly, only the automatic setting of the enlargement mode is performed before step S252 is reached.

The automatic setting from step S236 through S250 relates to automatic setting of comparatively general modes such as an enlargement mode and a white-black reversal mode. By contrast, steps S252 through S254 are provided to select and automatically set, according to the circumstances, one of a plurality of modes (including at least specific modes under specific conditions and a standard mode set specifically for the user) that are custom-set for a particular user to suit his symptoms such as impaired light or dark adaptation and an abnormal visual field. Specifically, at step S252, whether a condition is one that was custom-set is checked, and if so, an automatic custom mode setting process at step S254 is initiated, where a mode setting is automatically changed, and the flow then proceeds to step S256. On the other hand, if, at step S252, a condition is not detected being a custom-set one, the flow proceeds directly to step S256, where the currently set mode is maintained.

At step S256, whether or not movement acceleration has been detected is checked. If movement acceleration has been detected, the flow proceeds to step S258, where an automatic return to the standard mode is made, and the flow ends. On the other hand, if, at step S256, no movement acceleration is detected, the currently set mode is maintained, and the flow ends. If, at step S256, movement acceleration is detected, it can indicate that, for example, a person who was sitting on a chair and reading a book or doing handwork has stood up and started to walk, and maintaining the enlargement mode or the white-black reversal mode in such a situation can be dangerous; therefore, at step S258, an automatic return to the standard mode is made. The standard mode is the real-scale mode or the wide mode set at step S234 or S238. The standard mode may be custom-set beforehand to suit a particular user.

The various features of the examples described above are not limited to those particular embodiments, but may be implemented in any other embodiments so long as they provide their benefits. Although in the present description, for simplicity's sake, the description and illustration of each embodiment concentrate on features different from the other embodiments, needless to say, embodiments are also possible where features described in connection with different embodiments coexist, where those features are replaced with other features, or where a plurality of features are combined together.

EXAMPLE 4

Figure 11:
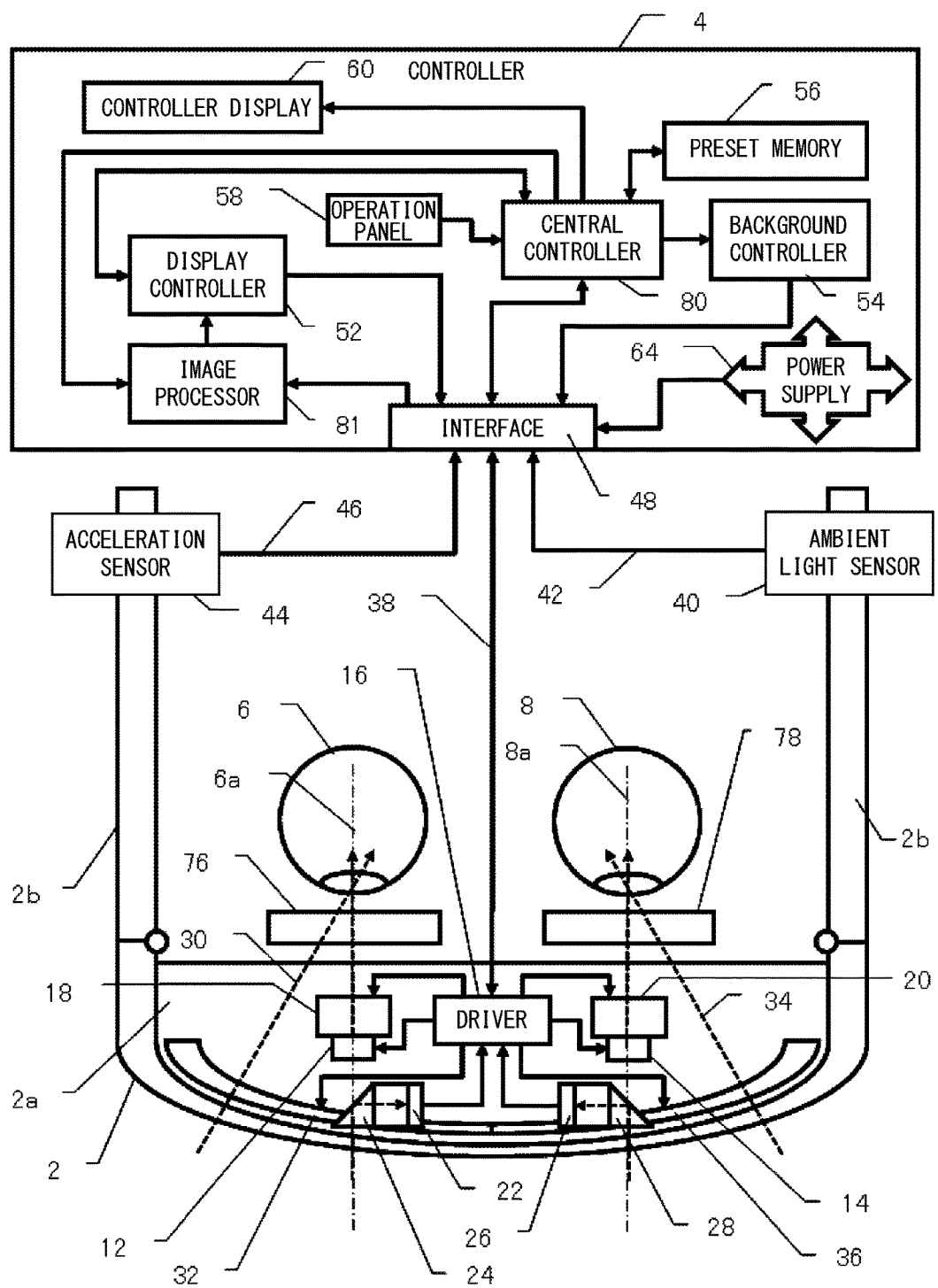
FIG. 11 is a block diagram showing the overall configuration of a vision aid system in Example 4 embodying the present invention (Example 4)

FIG. 11 is a block diagram showing the overall configuration of a vision aid system in Example 4 embodying the present invention. The configuration of Example 4 in FIG. 11 has much in common with Example 1 in FIG. 1; accordingly, the same parts are identified with the same reference signs, and no overlapping description will be repeated. A first difference of Example 4 from Example 1 is that it is configured to be usable without the use of ordinary eyeglasses 10. That is, adjustment of the dioptric power for near-sightedness and far-sightedness is achieved through adjustment of the focus of the right-eye and left-eye eyepiece optical systems 18 and 20; astigmatism is corrected with a right-eye toric lens 76 and a left-eye toric lens 78 which are removably inserted. The right-eye and left-eye toric lenses 76 and 78 are individually interchangeable to suit the user's dioptric power, and are removable whenever unnecessary. With the right-eye and left-eye toric lenses 76 and 78 inserted, they are rotated about the lines of sight 6a and 8a respectively to achieve correction that suits the axial angle of the user's astigmatism. A second difference of Example 4 from Example 1 is that a central controller 80 and an image processor 81 execute unique functions, which will be described later.

Figure 12A:
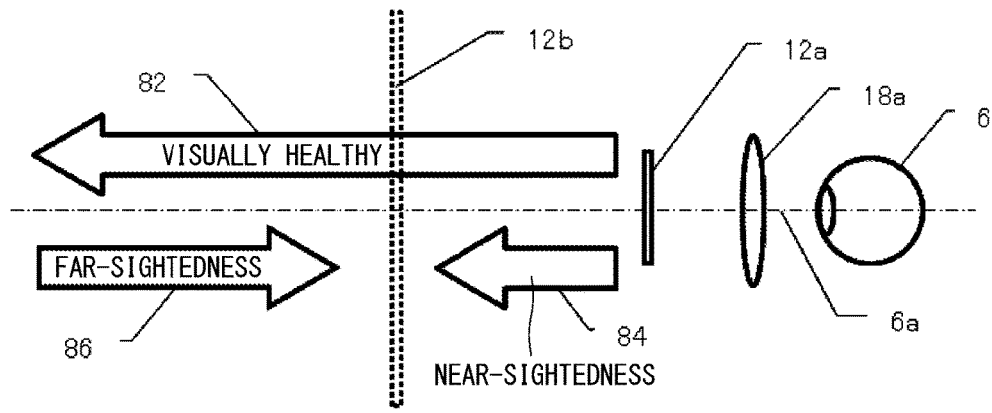
FIG. 12A is a schematic sectional view (a standard state) explaining the principle of dioptric power adjustment in the eyepiece optical systems in Example 4.
Figure 12B:
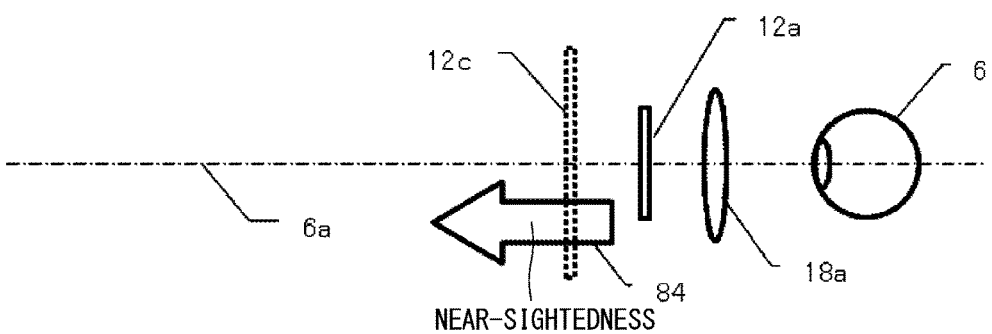
FIG. 12B is a schematic sectional view (a short-sightedness correcting state) explaining the principle of dioptric power adjustment in the eyepiece optical systems in Example 4.
Figure 12C:
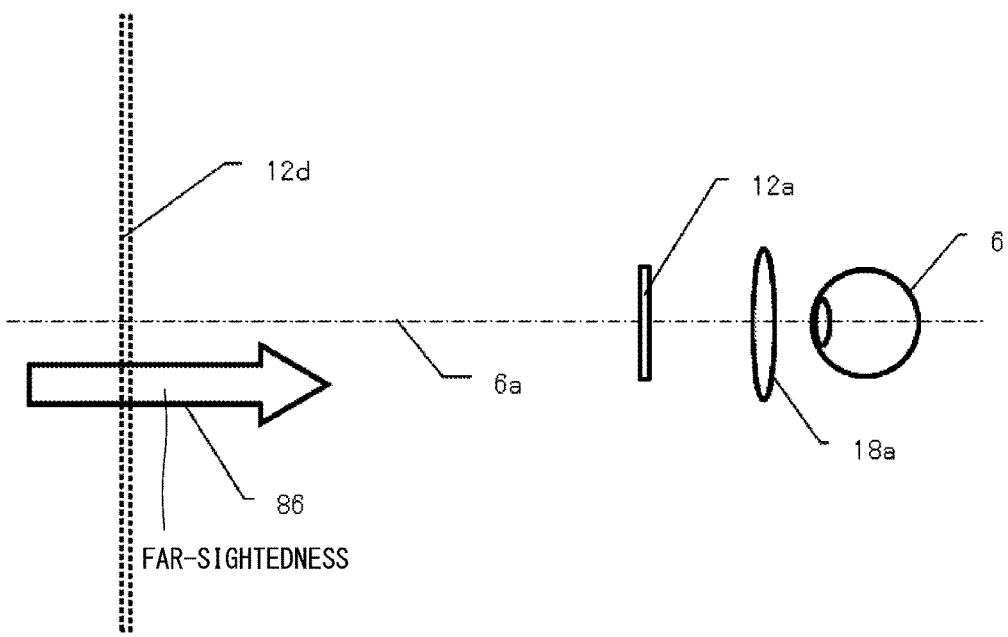
FIG. 12C is a schematic sectional view (a far-sightedness correcting state) explaining the principle of dioptric power adjustment in the eyepiece optical systems in Example 4.

FIGS. 12A to 12C are schematic sectional diagrams explaining the principle of dioptric power adjustment for near-sightedness or far-sightedness in the eyepiece optical systems 18 and 20 in Example 4. For simplicity's sake, illustration and description will be given only for the right eye 6, and the same apply equally to the left eye 8. In FIG. 12A, an eyepiece lens 18a in the right-eye eyepiece optical system 18 is movable for dioptric power adjustment between a display surface 12a and the right eye 6 along the right-eye line of sight 6a. In the state in FIG. 12A, the eyepiece lens 18a is set at a standard position. In this state, the virtual image 12b of the display surface 12a is located within a visual acuity range 82 of the visually healthy. On the other hand, in the state in FIG. 12A, the position of the virtual image 12b of the display surface 12a falls outside either of a visual acuity range 84 of the near-sighted and a visual acuity range 86 of the far-sighted.

In FIG. 12B, the dioptric power has been adjusted by shifting the eyepiece lens 18a toward the display surface 12a so that the display virtual image 12c is located within the visual acuity range 84 of the near-sighted. In FIG. 12C, the dioptric power has been adjusted by shifting the eyepiece lens 18a toward the right eye 6 so that the display virtual image 12d is located within the visual acuity range 86 of the far-sighted.

FIGS. 13A to 13C to FIGS. 19A to 19C are diagrams explaining the relationship between parallax and convergence angle as observed mainly in the imaging and displaying of a 3D (three-dimensional) image, based on a study of different states in Example 4 in relation to the relationship in FIGS. 12A to 12C respectively. As will be described in detail below, in Example 4, an imaging system and a display system are each configured to fulfill predetermined conditions so that 3D display is possible with hardly any sense of unnaturalness over the entire ranges of dioptric power adjustment for near- and far-sightedness, of object distance change, and of enlargement and reduction (widening where a peripheral image is involved) of the display image. In FIGS. 13A to 13C to FIGS. 17A to 17C, for simplicity's sake, a single object point and the eyes' convergence angle are studied; in FIGS. 18A to 18B and FIGS. 19A to 19B, the reality of vision based on the convergence angle is studied with the displayed image enlarged and reduced, respectively. The process by which the brain recognizes a 3D image depends not only on one element like the eyes' convergence angle with respect to a single object point but also greatly on, for example, parallax information on a plurality of object points at different distances. However, the elements studied do not contradict the results of comprehensive 3D recognition by eye movement and the brain.

Figure 13A:
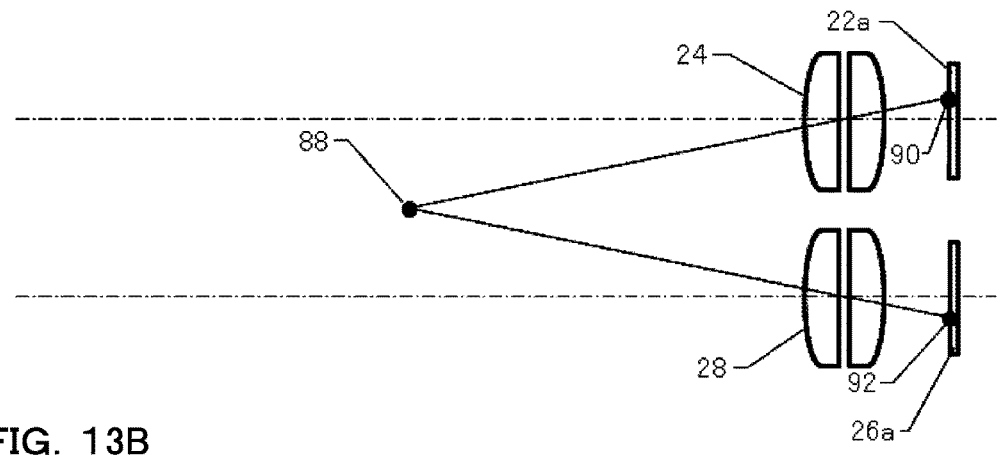
FIG. 13A is a schematic diagram (a basic configuration) as to the imaging and displaying of a 3D image in Example 4.
Figure 13B:
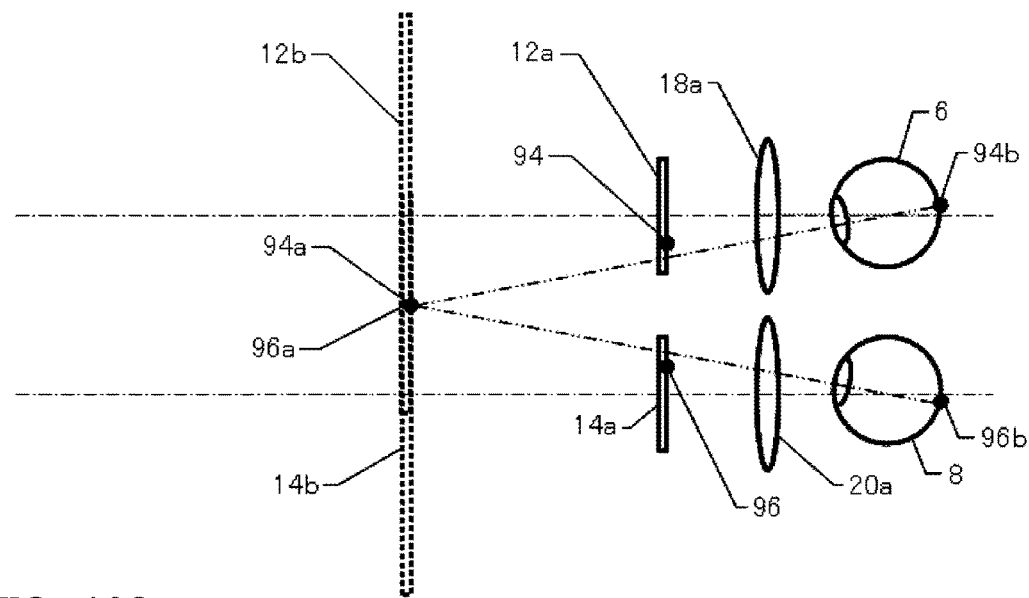
FIG. 13B is a schematic diagram (a display state) as to the imaging and displaying of a 3D image in Example 4.
Figure 13C:
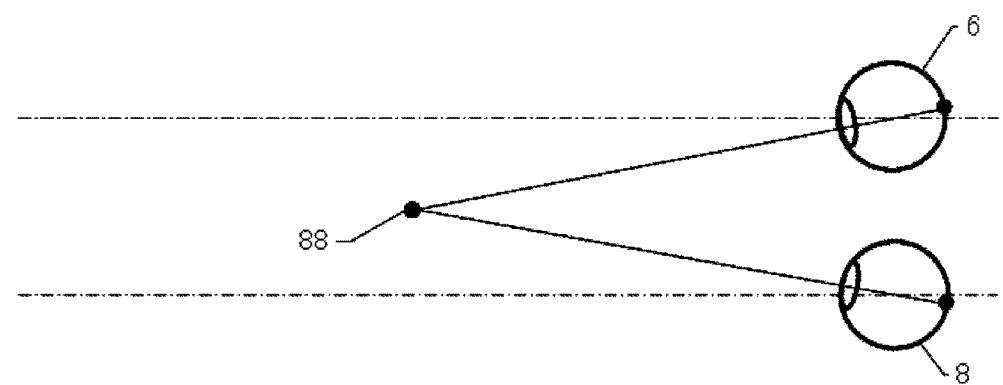
FIG. 13C is a schematic diagram (a naked-eye real-view state) as to the imaging and displaying of a 3D image in Example 4.

FIGS. 13A to 13C show the basic configuration for imaging and displaying a 3D image in Example 4. FIG. 13A shows the basic configuration of a parallel binocular imaging system composed of a right-eye deflecting zoom lens optical system 24 and a left-eye deflecting zoom lens optical system 28. For simplicity's sake, the optical paths that are bent in reality are illustrated as straightened optical paths that are equivalent to them. As will be clear from FIG. 13A, the optical axes (indicated by broken lines) of the right-eye and left-eye deflecting zoom lens optical systems 24 and 28 are parallel to each other, and their interval (axis-to-axis interval, referred to as an optical axis interval) is set at an average human interpupillary distance. Moreover, the right-eye and left-eye deflecting zoom lens optical systems 24 and 28 are both set at a standard focal length, and their foci are adjusted to be on an object point 88 located at a standard distance. The standard distance of the object point 88 is set equal to the distance of the position of the virtual image 12b of the display surface 12a in FIG. 12A. In this configuration, parallax arises with respect to the object point 88 as seen from the right-eye and left-eye deflecting zoom lens optical systems 24 and 28, and thus the image point 90 imaged on the imaging surface 22a of the right-eye image sensor 22 and the image point 92 imaged on the imaging surface 26a of the right-eye image sensor 26 are located at positions displaced from the respective optical axes in the opposite directions. This is imaged, as parallax information on the object point 88, by the right-eye and left-eye image sensors 22 and 26.

In FIG. 13B, by use of a parallel binocular display of which the interpupillary distance equals the interval between the optical axes of parallel binocular lenses (the right-eye and left-eye deflecting zoom lens optical systems 24 and 28), image information imaged by the right-eye and left-eye image sensors 22 and 26 in FIG. 13A are displayed on the right-eye and left-eye display surfaces 12a and 14a respectively. In FIG. 13B, the positions of the right-eye display surface 12a and the right-eye eyepiece lens 18a are set as in FIG. 12A, and so are the positions of the left-eye display surface 14a and the left-eye eyepiece lens 20a. Thus, the virtual image 12b of the display surface 12a and the virtual image 14b of the display surface 14a are seen at the same position.

Moreover, in FIG. 13A, the image point 90 imaged on the imaging surface 22a and the image point 92 imaged on the imaging surface 26a are both real images that are each inverted upside down and reversed left to right. Accordingly, when these images are displayed on the right-eye and left-eye display surfaces 12a and 14a and their virtual images are observed, they are displayed each 180 degrees rotated upside down and left to right to appear as erect images. As a result, the image information of the image points 90 and 92 on the imaging surfaces 22a and 26a is displayed as display points 94 and 96, respectively, on the right-eye and left-eye display surfaces 12a and 14a.

In this way, the right-eye and left-eye display surfaces 12a and 14a on which the display points 94 and 96 are respectively displayed are observed, through the right-eye and left-eye eyepiece lenses 18a and 20a, as the virtual images 12b and 14b of the display surfaces on which virtual-image display points 94a and 96a are respectively displayed. Here, the central controller 80 controls the image processor 81 to perform shift adjustment on the display points 94 and 96 so that the virtual-image display points 94a and 96a coincide. FIG. 13B shows a state where, as a result of the right and left eyes 6 and 8 gazing at the virtual-image display points 94a and 96a described above, real images 94b and 96b of the virtual-image display points 94a and 96a are imaged at the centers of the retinae of the right and left eyes 6 and 8 respectively. The gaze produces a convergence angle between the right and left eyes 6 and 8, and produces the sense of distance to the coincident virtual-image display points 94a and 96a.

FIG. 13C shows a state of the convergence angle between the right and left eyes 6 and 8 as observed when a visually healthy person really sees the object point 88 in FIG. 13A with naked eyes. The convergence angle in FIG. 13B approximately equals that in FIG. 13C, and thus observation in FIG. 13B gives the user the same perception as does observation in FIG. 13C. The description thus far concerns with a visually healthy person, and corresponds, in terms of visual acuity range, the state described with reference to FIG. 12A.

Figure 14A:
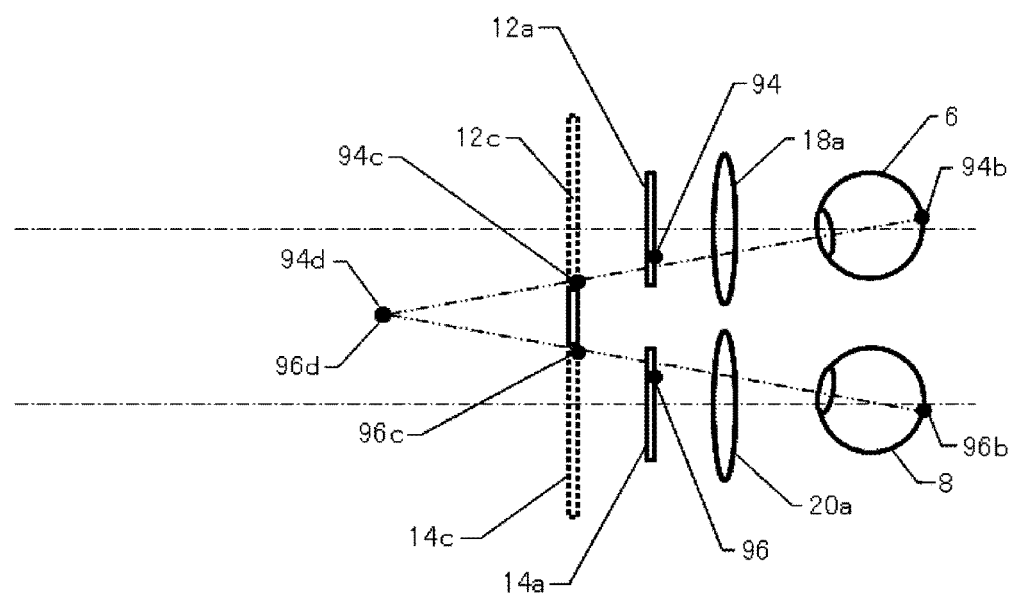
FIG. 14A is a schematic diagram (a display state) as to a near-sighted person in Example 4.
Figure 14B:
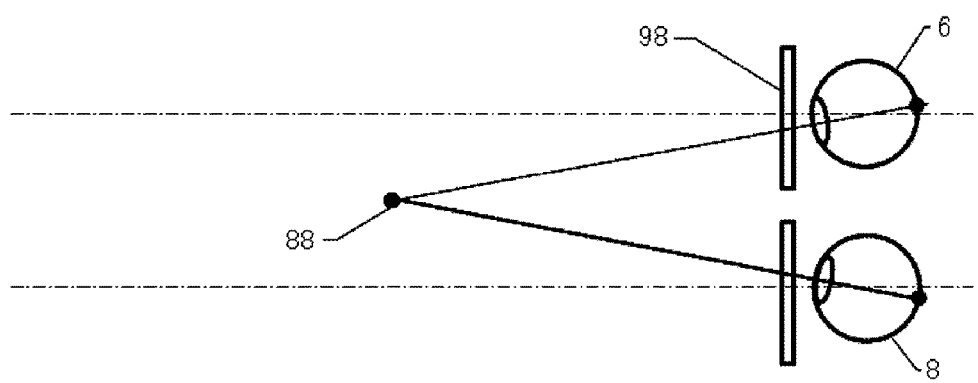
FIG. 14B is a schematic diagram (a corrected real-view state) as to a near-sighted person in Example 4.

In FIGS. 14A and 14B, a similar study is done in Example 4 with a near-sighted person. As explained with reference to FIG. 12A, the virtual images 12b and 14b of the right-eye and left-eye display surfaces 12a and 14a in the state in FIG. 13B are both located outside the visual acuity range 84 of the near-sighted, and cannot be seen clearly. Accordingly, in FIG. 14A, as in FIG. 12B, the dioptric power is adjusted by shifting the right-eye and left-eye eyepiece lenses 18a and 20a toward the right-eye and left-eye display surfaces 12a and 14a so that the virtual images 12c and 14c of the right-eye and left-eye display surfaces 12a and 14a are both located within the visual acuity range 84 of the near-sighted. The right-eye and left-eye display surfaces 12a and 14a and the display points 94 and 96 displayed on them are the same as those in FIG. 13B.

In FIG. 14A, as in FIG. 12B, the virtual image 12c of the display surface 12a on which the display point 94 is displayed and the virtual image 14c of the display surface 14a on which the display point 96 is displayed are closer to the right and left eyes 6 and 8 respectively, and are located within the visual acuity range 84 of the near-sighted. However, at this time, virtual-image display points 94c and 96c that appear to be displayed on the virtual images 12c and 14c of the right-eye and left-eye display surfaces 12a and 14a respectively do not coincide on the virtual images 12c and 14c located within the visual acuity range 84. However, trying to see the virtual-image display points 94c and 96c as coincident points, the right and left eyes 6 and 8 assume a convergence angle that permits the real images 94b and 96b of the virtual-image display points 94c and 96c to be imaged at the centers of the retinae of the right and left eyes 6 and 8 respectively. As a result, what is being seen is perceived as coincident points 94d and 96d.

FIG. 14B shows a state of the convergence angle between the right and left eyes 6 and 8 as observed when a near-sighted person really sees the object point 88 in FIG. 13A with concave-lens glasses 98 worn for correction in everyday life. The convergence angle in FIG. 14A approximately equals the convergence angle in FIG. 14B, and thus observation of the coincident points 94d and 96d in FIG. 14A, where the dioptric power is adjusted for the naked eye, gives the user the same perception as does observation of the object point 88 with glasses 98 worn in everyday life as in FIG. 14B. Strictly speaking, the positions of the coincident points 94d and 96d in FIG. 14A differ from those of the virtual-image display points 94a and 96a in FIG. 13B, but because the difference is slight, it is possible to omit shifting and correcting the positions of the display points 94 and 96 displayed on the right-eye and left-eye display surfaces 12a and 14a according to dioptric power adjustment between FIGS. 13B and 14B.

Figure 15A:
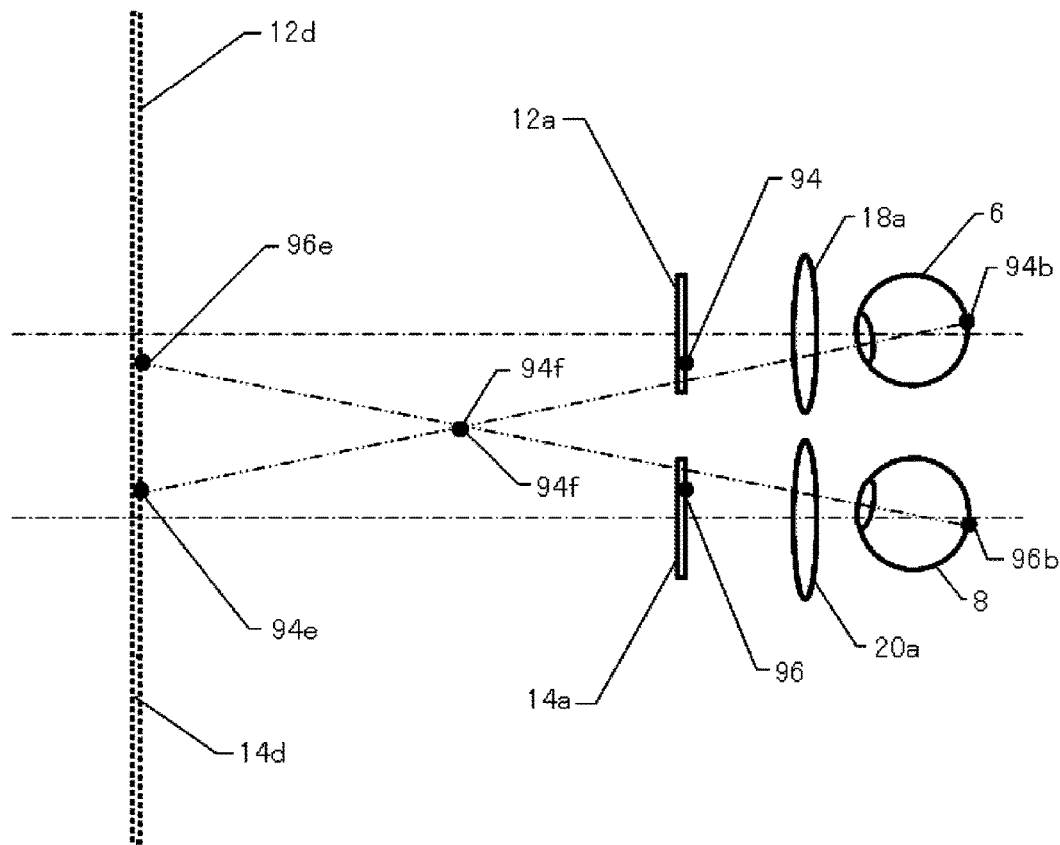
FIG. 15A is a schematic diagram (a display state) as to a far-sighted person in Example 4.
Figure 15B:
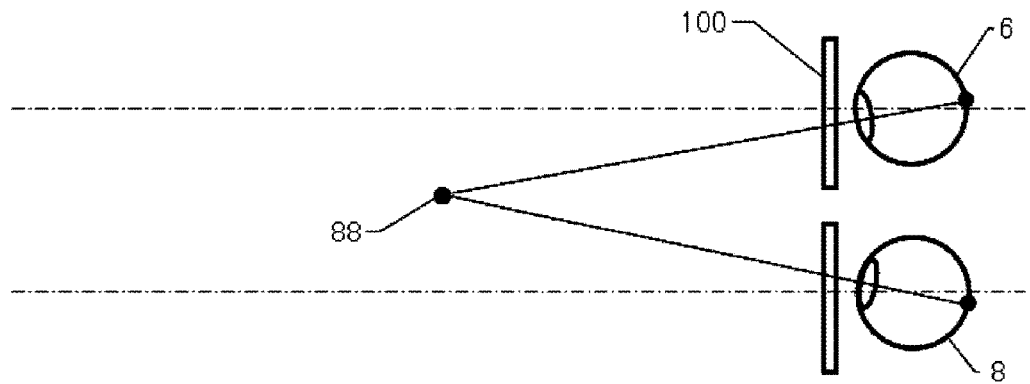
FIG. 15B is a schematic diagram (a corrected real-view state) as to a far-sighted person in Example 4.

In FIGS. 15A and 15B, a similar study is done in Example 4 with a far-sighted person. As explained with reference to FIG. 12A, the virtual images 12b and 14b of the right-eye and left-eye display surfaces 12a and 14a in the state in FIG. 13B are both located outside the visual acuity range 86 of the far-sighted, and cannot be seen clearly. Accordingly, in FIG. 15A, as in FIG. 12C, the dioptric power is adjusted by shifting the right-eye and left-eye eyepiece lenses 18a and 20a toward the right and left eyes 6 and 8 so that the virtual images 12d and 14d of the right-eye and left-eye display surfaces 12a and 14a are both located within the visual acuity range 86 of the far-sighted. The right-eye and left-eye display surfaces 12a and 14a and the display points 94 and 96 displayed on them are the same as those in FIG. 13B.

In FIG. 15A, as in FIG. 12C, the virtual image 12d of the display surface 12a on which the display point 94 is displayed and the virtual image 14d of the display surface 14a on which the display point 96 is displayed are farther away from the right and left eyes 6 and 8 respectively, and are located within the visual acuity range 86 of the far-sighted. However, at this time, virtual-image display points 94e and 96e that appear to be displayed on the virtual images 12d and 14d of the right-eye and left-eye display surfaces 12a and 14a respectively do not coincide on the virtual images 12d and 14d located within the visual acuity range (their positions are crossed and reversed relative to each other). However, trying to see the virtual-image display points 94e and 96e as coincident points, the right and left eyes 6 and 8 assume a convergence angle that permits the real images 94b and 96b of the virtual-image display points 94e and 96e to be imaged at the centers of the retinae of the right and left eyes 6 and 8 respectively. As a result, what is being seen is perceived as coincident points 94f and 96f FIG. 15B shows a state of the convergence angle between the right and left eyes 6 and 8 as observed when a far-sighted person really sees the object point 88 in FIG. 13A with convex-lens glasses 100 worn for correction in everyday life. The convergence angle in FIG. 15A too approximately equals the convergence angle in FIG. 15B, and thus observation of the coincident points 94f and 96f in FIG. 15A, where the dioptric power is adjusted for the naked eye, gives the user the same perception as does observation of the object point 88 with glasses 100 worn in everyday life as in FIG. 15B. Strictly speaking, the positions of the coincident points 94f and 96f in FIG. 15A differ from those of the virtual-image display points 94a and 96a in FIG. 13B, but, as with near-sightedness, it is possible to omit shifting and correcting the positions of the display points 94 and 96 displayed on the right-eye and left-eye display surfaces 12a and 14a according to dioptric power adjustment.

The above has been a description of how a visually healthy person, a short-sighted person, and a long-sighted person see the display on the right-eye and left-eye display surfaces 12a and 14a based on the same image information taken in FIG. 13A. As described above, in Example 4, parallax information on the object point 88 is obtained by a parallel binocular imaging system of which the interval is set at an average human interpupillary distance. Then, the image information including the parallax information is displayed on a parallel binocular display of which the interpupillary distance equals the interval between the optical axes of the parallel binocular imaging system so that, with the convergence angle of the eyes trying to see the object points on the right and left display at coincident points, binocular vision is achieved. Then, through dioptric power adjustment, a short- or long-sighted person is coped with so as to be presented with reproduction similar to that presented to a visually healthy person.

Next, with reference to FIGS. 16A to 16C and FIGS. 17A to 17C, a description will be given of a case where the position of an object point differs from that of the object point 88 set equal to the distance of the position of the virtual image 12b of the display surface 12a. For simplicity's sake, only a visually healthy person will be dealt with. As for a short- or long-sighted person, an understanding will be obtained similarly with reference to FIGS. 14A and 14B and FIGS. 15A and 15B.

Figure 16A:
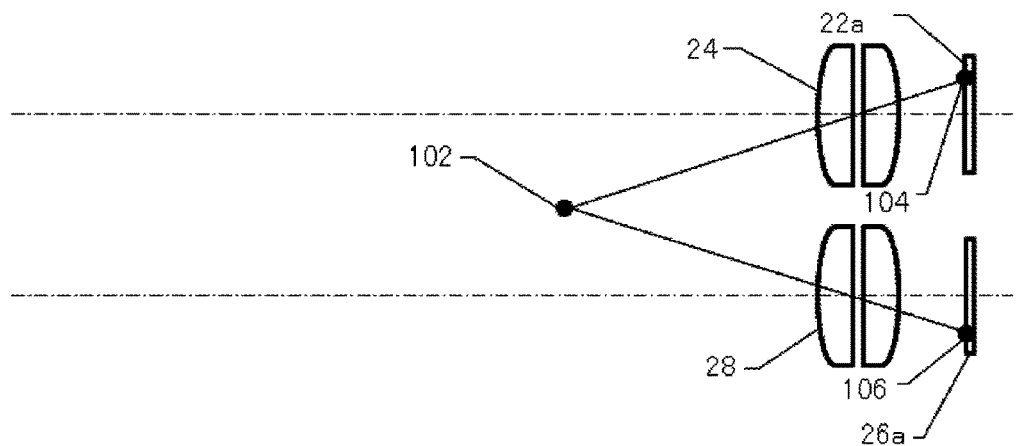
FIG. 16A is a schematic diagram (a basic configuration) as to a close object point in Example 4.
Figure 16B:
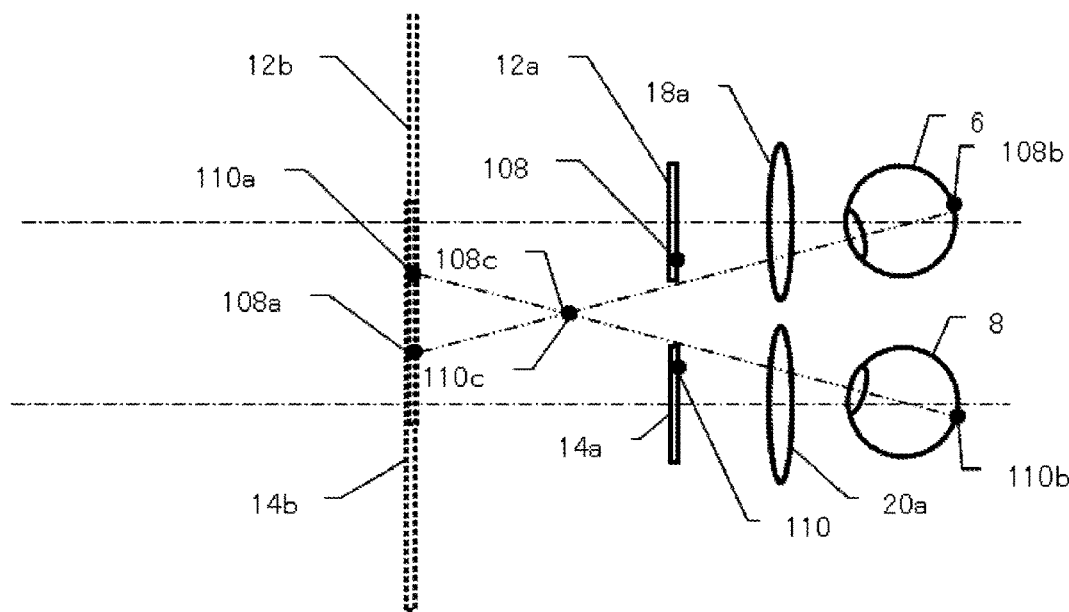
FIG. 16B is a schematic diagram (a display state) as to a close object point in Example 4.
Figure 16C:
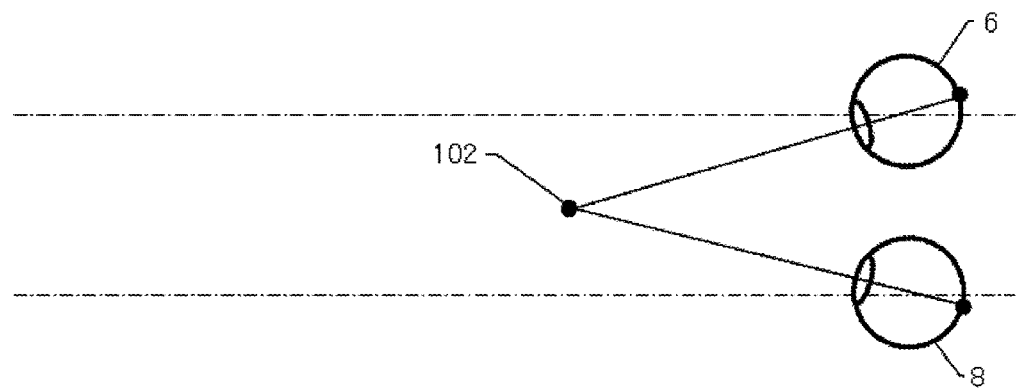
FIG. 16C is a schematic diagram (a naked-eye real-view state) as to a close object point in Example 4.

FIGS. 16A to 16C, though similar to FIGS. 13A to 13C, show a case where, as shown in FIG. 16A, the foci of the right-eye and left-eye deflecting zoom lens optical systems 24 and 28 are so adjusted as to be on a close object point 102 which is closer than the object point 88 at the standard distance in FIG. 13A. As will be described later, the close object point 102 is assumed to be located within the visual acuity range of a visually healthy person. In this state, the parallax with respect to the close object point 102 as seen from the right-eye and left-eye deflecting zoom lens optical systems 24 and 28 is larger than in the case shown in FIG. 13A, and thus the positions of the image points 104 and 106 imaged on the imaging surfaces 22a and 26a of the right-eye and left-eye image sensors 22 and 26 are displaced greatly from the respective optical axes in the opposite directions.

This is imaged, as parallax information on the close object point 102, by the right-eye and left-eye image sensors 22 and 26.

In FIG. 16B, the image information imaged by the right-eye and left-eye image sensors 22 and 26 in the state in FIG. 16A is displayed on the right-eye and left-eye display surfaces 12a and 14a respectively. In FIG. 16B, the positions of the right-eye display surface 12a and the right-eye eyepiece lens 18a are set similarly as in FIG. 12A, and so are the positions of the left-eye display surface 14a and the left-eye eyepiece lens 20a. In this respect, FIG. 16B is the same as FIG. 13B.

However, due to the close object point 102 being closer, the display points 108 and 110 displayed on the right-eye and left-eye display surfaces 12a and 14a are displaced greatly from the center of display in the opposite directions. Accordingly, when the right-eye and left-eye display surfaces 12a and 14a on which those display points 108 and 110 are respectively displayed are seen through the right-eye and left-eye eyepiece lenses 18a and 20a as virtual images 12b and 14b of the right-eye and left-eye display surfaces 12a and 14a respectively, the virtual-image display points 108a and 110a on the virtual images do not coincide (their positions are crossed and reversed relative to each other). However, trying to see those virtual-image display points 108a and 110a as coincident points, the right and left eyes 6 and 8 assume such a tense (large) convergence angle that real images 108b and 110b of the virtual-image display points 108a and 110a are imaged at the centers of the retinae of the right and left eyes 6 and 8. As a result, what is seen is perceived to be coincident points 108c and 110c located at a closer distance.

FIG. 16C shows a state of the convergence angle of the right and left eyes 6 and 8 as observed when a visually healthy person really sees the close object point 102 in FIG. 16A with naked eyes. As mentioned above, the close object point 102 is located within the visual acuity range of the visually healthy. The convergence angle in FIG. 16B approximately equals the convergence angle in FIG. 16C, and thus observation of the coincident points 108c and 110c in FIG. 16B gives the user the same perception as does observation of the close object point 102 in FIG. 16C.

Figure 17A:
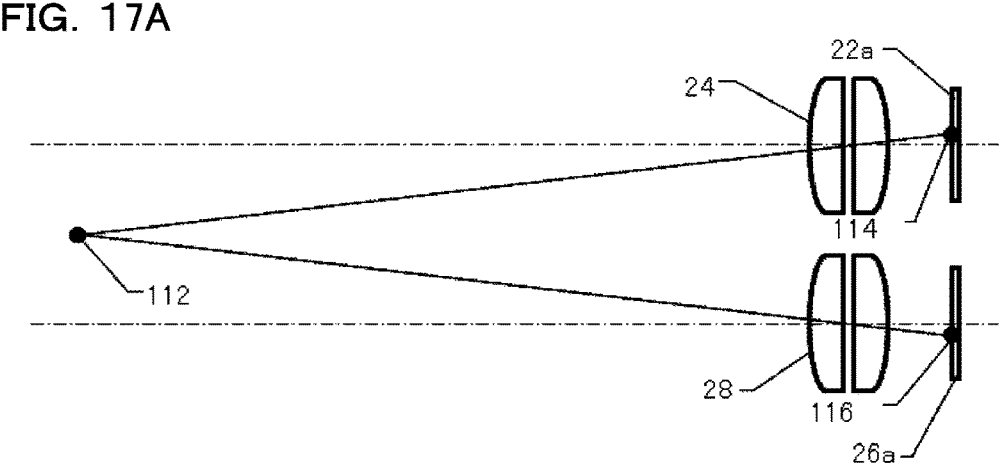
FIG. 17A is a schematic diagram (a basic configuration) as to a far object point in Example 4.
Figure 17B:
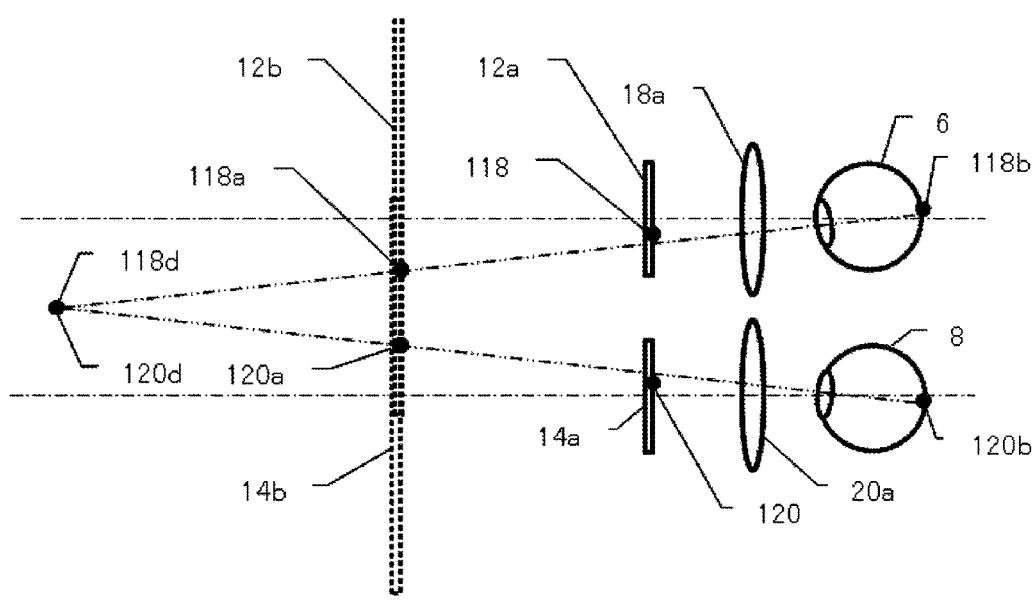
FIG. 17B is a schematic diagram (a display state) as to a far object point in Example 4.
Figure 17C:
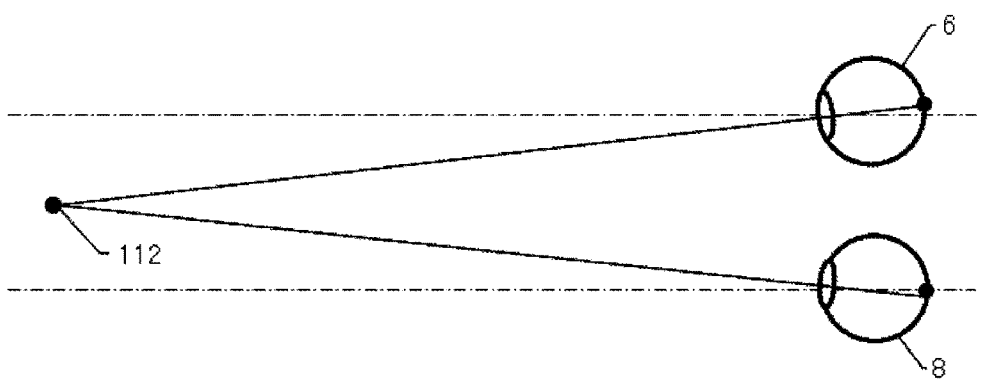
FIG. 17C is a schematic diagram (a naked-eye real-view state) as to a far object point in Example 4.

FIGS. 17A to 17C, though similar to FIGS. 13A to 13C and to FIGS. 16A to 16C, show a case where, as shown in FIG. 17A, the foci of the right-eye and left-eye deflecting zoom lens optical systems 24 and 28 are so adjusted as to be on a far object point 112 which is farther away than the object point 88 at the standard distance in FIG. 13A. The far object point 112 too is assumed to be located within the visual acuity range of a visually healthy person. In this state, the parallax with respect to the far object point 112 as seen from the right-eye and left-eye deflecting zoom lens optical systems 24 and 28 is smaller than in the case shown in FIG. 13A, and thus the positions of the image points 114 and 116 imaged on the imaging surfaces 22a and 26a of the right-eye and left-eye image sensors 22 and 26 are, though displaced, closer to the optical axes. This is imaged, as parallax information on the far object point 112, by the right-eye and left-eye image sensors 22 and 26.

In FIG. 17B, the image information imaged by the right-eye and left-eye image sensors 22 and 26 in the state in FIG. 17A is displayed on the right-eye and left-eye display surfaces 12a and 14a respectively. In FIG. 17B, the positions of the right-eye display surface 12a and the right-eye eyepiece lens 18a are set similarly as in FIG. 12A, and so are the positions of the left-eye display surface 14a and the left-eye eyepiece lens 20a. In this respect, FIG. 17B is the same as FIG. 13B and 16B.

However, due to the far object point 112 being farther away, the display points 118 and 120 displayed on the right-eye and left-eye display surfaces 12a and 14a are closer to the center of display. Accordingly, when the right-eye and left-eye display surfaces 12a and 14a on which those display points 118 and 120 are respectively displayed are seen through the right-eye and left-eye eyepiece lenses 18a and 20a as virtual images 12b and 14b of the right-eye and left-eye display surfaces 12a and 14a respectively, the virtual-image display points 118a and 120a on the virtual images do not coincide. However, trying to see those virtual-image display points 118a and 120a as coincident points, the right and left eyes 6 and 8 assume such a slack (small) convergence angle that real images 118b and 120b of the virtual-image display points 118a and 120a are imaged at the centers of retinae of the right and left eyes 6 and 8. As a result, what is seen is perceived to be coincident points 118c and 120c located at a farther distance.

FIG. 17C shows a state of the convergence angle of the right and left eyes 6 and 8 as observed when a visually healthy person really sees the far object point 112 in FIG. 17A with naked eyes. As mentioned above, the far object point 112 is located within the visual acuity range of the visually healthy. The convergence angle in FIG. 17B approximately equals the convergence angle in FIG. 17C, and thus observation of the coincident points 118d and 120d in FIG. 17B gives the user the same perception as does observation of the far object point 112 in FIG. 17C.

The configuration of Example 4, where image information imaged by a parallel binocular imaging system having mutually parallel optical axes of which the interval is set at an average human interpupillary distance is respectively displayed on a parallel binocular display of which the interpupillary distance equals the interval between the optical axes of the parallel binocular imaging system, achieves binocular vision with respect to objects at varying distances owing to the convergence angle of the eyes trying to see object points on right and left display as coincident points.

FIGS. 18A and 18B and FIGS. 19A and 19B are directed to cases where the central controller 80 controls the image processor 81 so as to enlarge and reduce (widen), respectively, the display images on the right-eye and left-eye display surfaces 12a and 14a, and show a study on the reality of vision obtained where enlargement and reduction are involved from the viewpoint of the convergence angle.

Figure 18A:
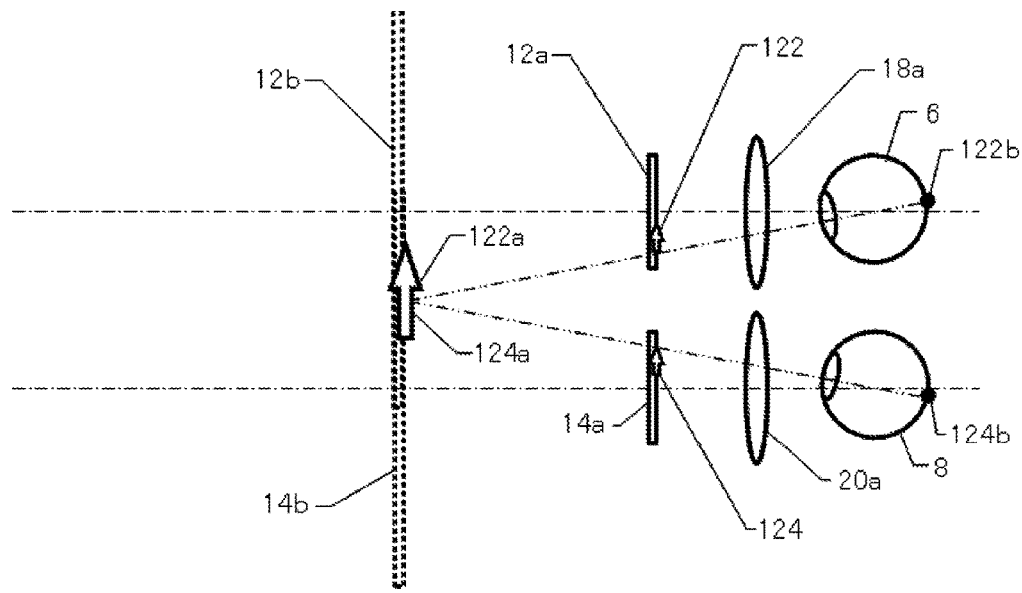
FIG. 18A is a schematic diagram (a standard magnification) as to display image enlargement in Example 4.
Figure 18B:
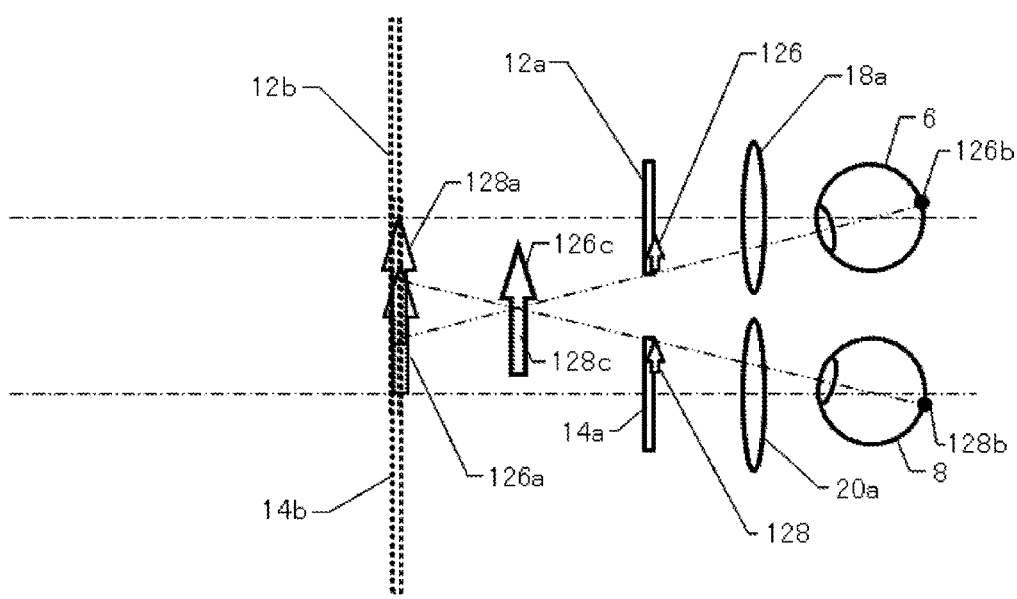
FIG. 18B is a schematic diagram (enlarged) as to display image enlargement in Example 4.

FIGS. 18A and 18B are directed to a case where the display images on the right-eye and left-eye display surfaces 12a and 14a are each enlarged. First, FIG. 18A shows a standard-magnification state before enlargement, corresponding to the state in FIG. 13B. Here, display images 122 and 124 are displayed on the right-eye and left-eye display surfaces 12a and 14a respectively (to illustrate the effect of enlargement and reduction, instead of points, dimensional images (hollow arrows) are shown here). As in FIG. 13B, the right-eye and left-eye display surfaces 12a and 14a on which the display images 122 and 124 are displayed are seen through the right-eye and left-eye eyepiece lenses 18a and 20a as virtual images 12b and 14b of the right-eye and left-eye display surfaces 12a and 14a on which the virtual-image display images 122a and 124a are displayed respectively. Here, as in FIG. 13B, the virtual-image display images 122a and 124a coincide. FIG. 18A shows a state where, as a result of the right and left eyes 6 and 8 gazing at those virtual-image display images 122a and 124a, real images 122b and 124b (of which only the positions are indicated by dots) of the virtual-image display images 122a and 124a are imaged at the centers of the retinae of the right and left eyes 6 and 8. As in FIG. 13B, the gaze produces the convergence angle between the right and left eyes 6 and 8, and produces the sense of distance to the coincident virtual-image display points 122a and 124a.

In contrast, FIG. 18B shows a case where the display images on the right-eye and left-eye display surfaces 12a and 14a are enlarged into enlarged display images 126 and 128 respectively. What is important here is, instead of enlarging the enlarged display images 126 and 128 themselves about their respective centers, to enlarge the entire images about central parts of the entire right t-eye and left-eye display surfaces 12a and 14a. Consequently, when the display images 122 and 124, which were not in central parts of the entire right-eye and left-eye display surfaces 12a and 14a in the state in FIG. 18A, become the enlarged display images 126 and 128 in FIG. 18B, they are not only enlarged but are also farther displaced to the opposite sides (away from the central parts of the respective display surfaces).

Accordingly, when the right-eye and left-eye display surfaces 12a and 14a on which the enlarged display images 126 and 128 are displayed are seen through the right-eye and left-eye eyepiece lenses 18a and 20 as the virtual images 12b and 14b of the right-eye and left-eye displays 12 and 14 respectively, virtual-image enlarged display images 126a and 128a on the virtual images do not coincide (their positions are crossed and reversed relative to each other). However, trying to see the virtual-image enlarged display images 126a and 128a as coincident points, the right and left eyes 6 and 8 assume such a tense (large) convergence angle that real images 126b and 128b (of which only the positions are indicated by dots) of the virtual-image enlarged display images 126a and 128a are imaged at the centers of the retinae of the right and left eyes 6 and 8 respectively. As a result, what is seen is perceived to be coincident images 126c and 128c located at a closer distance. Thus, the coincident images 126c and 128c are enlarged and in addition appear closer, providing the reality of a 3D (three-dimensional) image.

Figure 19A:
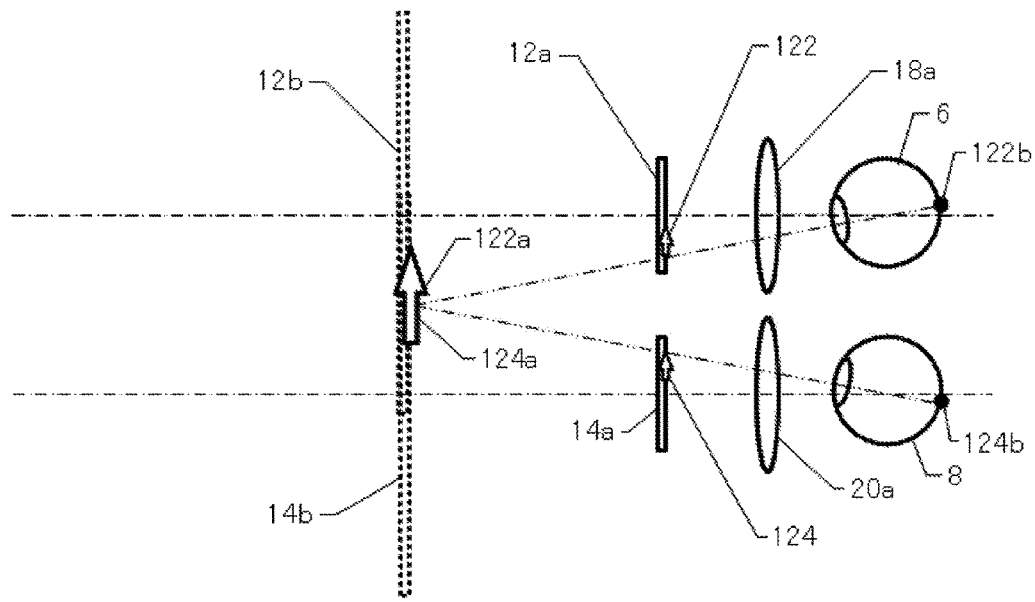
FIG. 19A is a schematic diagram (a standard magnification) as to display image reduction in Example 4.
Figure 19B:
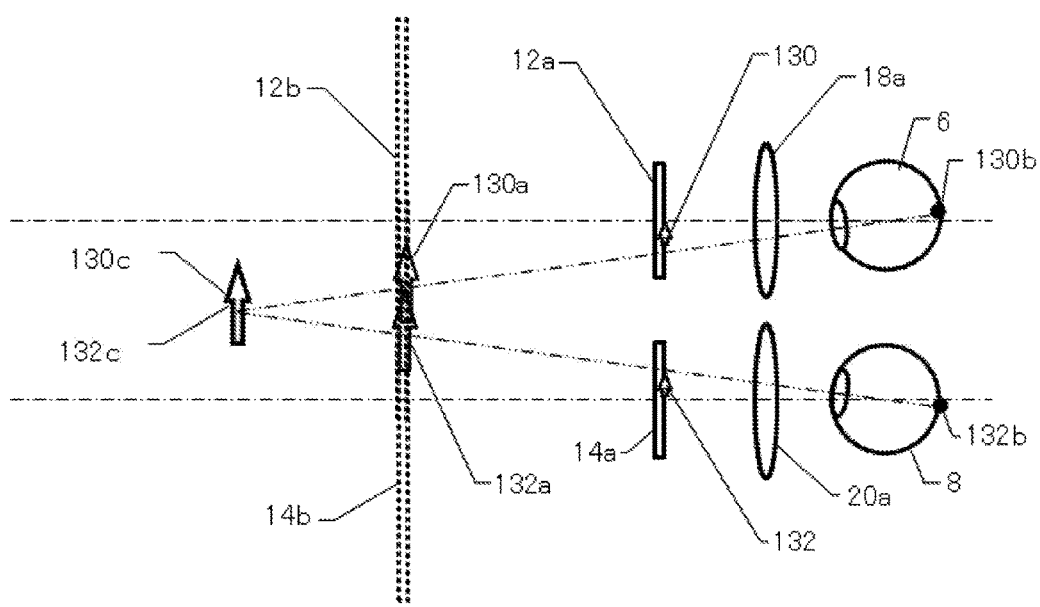
FIG. 19B is a schematic diagram (reduced) as to display image reduction in Example 4.

On the other hand, FIGS. 19A and 19B are directed to a caser where the display images on the right-eye and left-eye display surfaces 12a and 14a are reduced (or, in a case where there is a peripheral image, widened). FIG. 19A is the same as FIG. 18A, showing the standard magnification state before reduction.

In contrast, FIG. 19B shows a case where the display images on the right-eye and left-eye display surfaces 12a and 14a are reduced into reduced display images 130 and 132 respectively. What is important here as in FIG. 18B is, instead of reducing the reduced display images 130 and 132 themselves about their respective centers, to reduce the entire images about central parts of the entire right-eye and left-eye display surfaces 12a and 14a. Consequently, when the display images 122 and 124 in the state in FIG. 19A become the reduced display images 130 and 132 in FIG. 19B, they are not only reduced but also come closer to the central parts of the respective display surfaces.

Accordingly, when the right-eye and left-eye display surfaces 12a and 14a on which the reduced display images 130 and 132 are displayed are seen through the right-eye and left-eye eyepiece lenses 18a and 20 as the virtual images 12b and 14b of the right-eye and left-eye displays 12 and 14 respectively, virtual-image reduced display images 130a and 132a on the virtual images do not coincide. However, trying to see the virtual-image reduced display images 130a and 132a as coincident points, the right and left eyes 6 and 8 assume such a slack (small) convergence angle that real images 130b and 132b (of which only the positions are indicated by dots) of the virtual-image reduced display images 130a and 132a are imaged at the centers of the retinae of the right and left eyes 6 and 8 respectively. As a result, what is seen is perceived to be coincident images 130c and 132c located at a farther distance. Thus, the coincident images 130c and 132c are reduced and in addition appear farther away, providing the reality of a 3D image.

FIGS. 20A to 20C to FIGS. 22A to 22C explain the parallax and the convergence angle observed in a case employing an imaging system and a display system that are in a different relationship with each other than under the conditions described with reference to FIGS. 13A to 13C to FIGS. 19A to 19B.

EXAMPLE 5

Figure 20A:
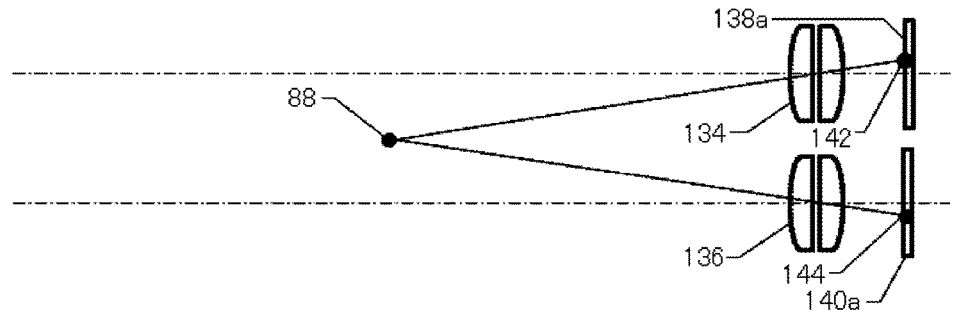
FIG. 20A is a schematic sectional view (a basic configuration) of Example 5 embodying the present invention (Example 5)
Figure 20B:
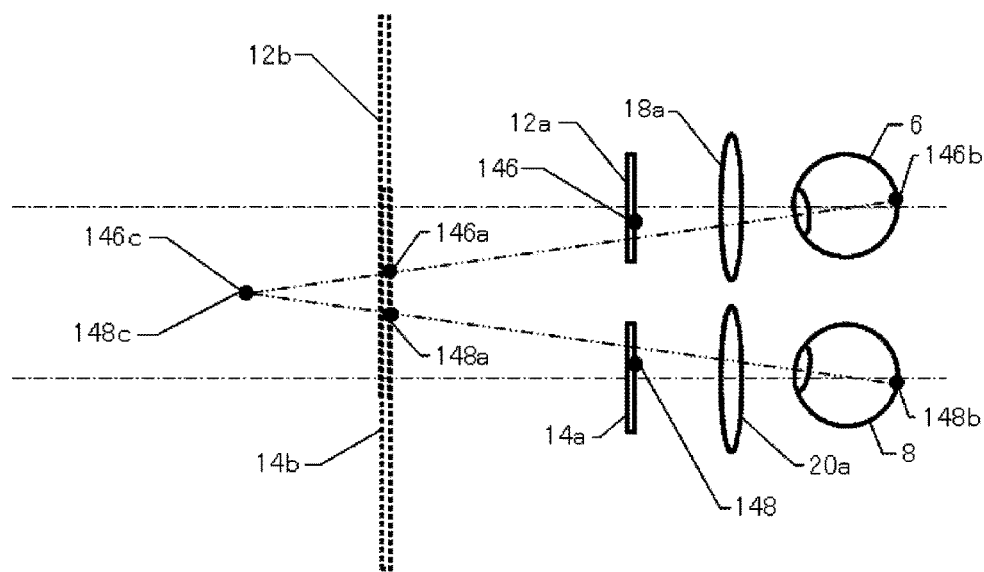
FIG. 20B is a schematic sectional view (with no shifting) of Example 5 embodying the present invention (Example 5)
Figure 20C:
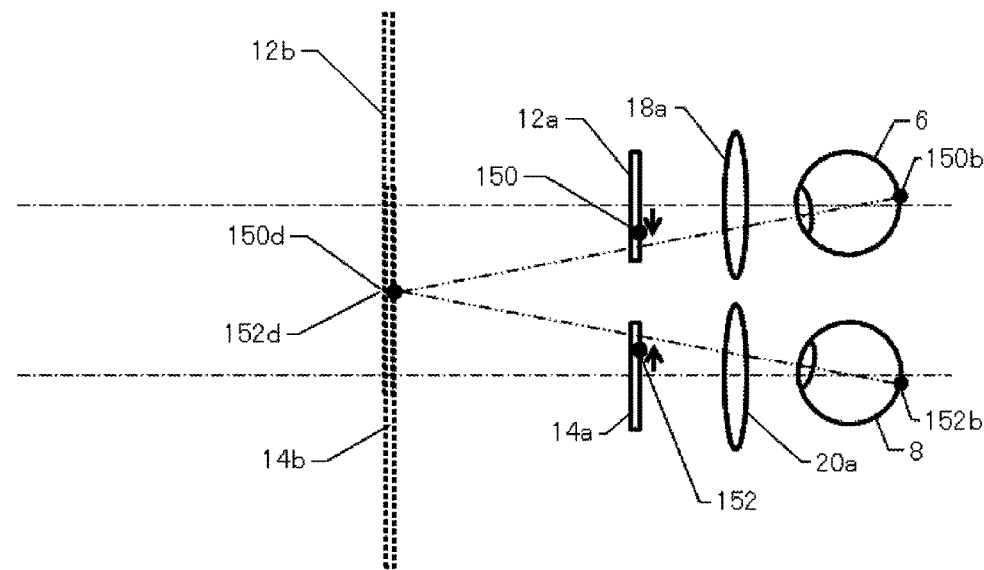
FIG. 20C is a schematic sectional view (with shifting) of Example 5 embodying the present invention (Example 5)

FIGS. 20A to 20C are schematic sectional views of Example 5 embodying the present invention. In Example 5 shown in FIGS. 20A to 20C to FIGS. 22A to 22C, image information taken by a compact parallel binocular imaging system having mutually parallel optical axes of which the interval is set smaller than an average human interpupillary distance is respectively displayed on a parallel binocular display of which the interval is set equal to an average human interpupillary distance. To follow is a description of processing in Example 5, where, as just mentioned, the parallel binocular imaging system and the parallel binocular display system have different optical axis intervals. Example 5 shares other features with Example 4, and accordingly, for detailed features, FIG. 11 is to be referred to auxiliarily.

FIG. 20A shows the basic configuration of a 3D parallel binocular imaging system composed of a right-eye deflecting zoom lens optical system 134 and a left-eye deflecting zoom lens optical system 136. As in FIG. 13A, for simplicity's sake, the optical paths are illustrated in a straightened form. As in Example 4, the optical axes of the right-eye and left-eye deflecting zoom lens optical systems 134 and 136 are parallel to each other, and their interval is smaller than an average human interpupillary distance. Incidentally, the right-eye and left-eye deflecting zoom lens optical systems 134 and 136 are both set at a standard focal distance, and their foci are so adjusted to be on an object point 88 located at a standard distance. The standard distance of the object point 88 is set equal to the distance of the position of the virtual image 12b of the right-eye display surface 12a.

The image points 142 and 144 imaged by those right-eye and left-eye deflecting zoom lens optical systems 134 and 136 on the imaging surfaces 138a and 140a of right-eye and left-eye image sensors are displaced from the respective optical axes in the opposite directions. However, the displacements are smaller than in FIG. 13A because the right-eye and left-eye deflecting zoom lens optical systems 134 and 136 have smaller optical axis intervals.

FIG. 20B shows a parallel binocular display of which the interpupillary distance equals an average human interpupillary distance as described above, configured as in FIG. 13B. However, if display on the right-eye and left-eye display surfaces 12a and 14a is performed based on image information in which the displacements of the image points 142 and 144 are small as in FIG. 20A, the display points 146 and 148 are closer to the centers of the respective display surfaces. Thus, when the right-eye and left-eye display surfaces 12a and 14a on which those display points 146 and 148 are displayed are seen as virtual images 12b and 14b of the right-eye and left-eye display surfaces 12a and 14a, virtual-image display points 146a and 148a do not coincide. Trying to see the virtual-image display points 146a and 148a as coincident points, the right and left eyes 6 and 8 assume such a slack (small) convergence angle that their real images 146b and 148b are imaged at the centers of the retinae of the right and left eyes 6 and 8. As a result, what is seen is perceived to be coincident points 146c and 148c located farther away than the object point 88. In this way, in a case where the optical axis intervals of the parallel binocular imaging system and the parallel binocular display system are not equal, the displayed coincident points 146c and 148c appear to be seen at a distance different from that of the object point 88 as the imaging target, and produces a sense of unnaturalness.

FIG. 20C shows a configuration for eliminating the sense of unnaturalness mentioned above. Specifically, as shown in FIG. 20C, the central controller 80 controls the image processor 81 so as to shift the display points on the right-eye and left-eye display surfaces 12a and 14a so that virtual-image display points 150d and 152d coincide on the virtual images 12b and 14b of the right-eye and left-eye display surfaces 12a and 14a. That is, as indicated by arrows in FIG. 20C, the display points 146 and 148 shown in FIG. 20B are shifted outward relative to the respective display surfaces up to display points 150 and 152 so that the virtual-image display points 150d and 152d coincide on the virtual images 12b and 14b of the right-eye and left-eye display surfaces 12a and 14a. Now, the state of the convergence angle is such that the displayed coincident points (virtual-image display points 150d and 152d) are seen at the same position as that of the object point 88 as the imaging target, producing no sense of unnaturalness.

EXAMPLE 6

Figure 21A:
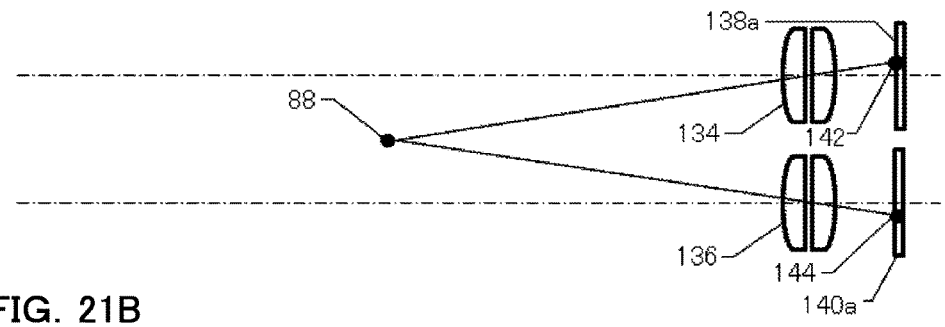
FIG. 21A is a schematic sectional view (a basic configuration) of Example 6 embodying the present invention (Example 6)
Figure 21B:
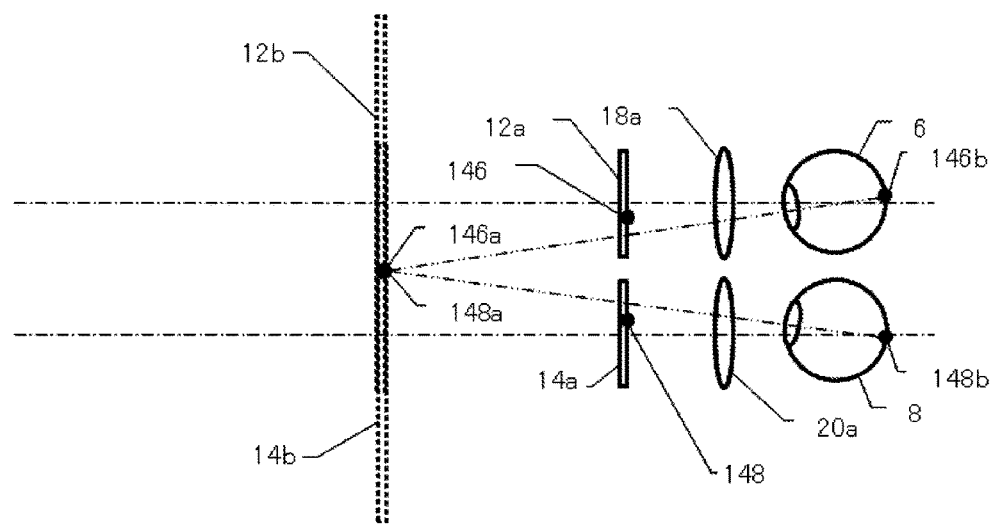
FIG. 21B is a schematic sectional view (with a reduced interpupillary distance) of Example 6 embodying the present invention (Example 6)
Figure 21C:
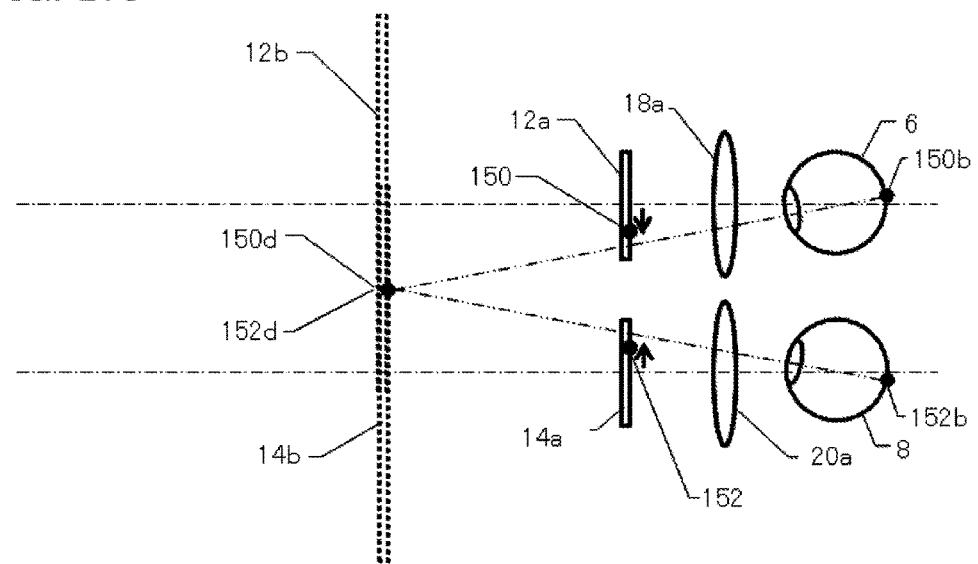
FIG. 21C is a schematic sectional view (with a increased interpupillary distance) of Example 6 embodying the present invention (Example 6)

FIGS. 21A to 21C are schematic sectional view of Example 6 embodying the present invention. In Example 6, a parallel binocular display is configured to have an adjustable interpupillary distance. Specifically, in Example 6 shown in FIGS. 21A to 21C, image information taken by a compact parallel binocular imaging system having mutually parallel optical axes of which the interval is set smaller than an average human interpupillary distance is respectively displayed on a parallel binocular display of which the interpupillary distance is adjustable.

FIG. 21A is the same as FIG. 20A. That is, also in Example 6, the interval between the optical axes of the right-eye and left-eye deflecting zoom lens optical systems 134 and 136 is smaller than an average human interpupillary distance, and the displacements of the image points 142 and 144 imaged on the imaging surfaces 138a and 140a of right-eye and left-eye image sensors are smaller than in FIG. 13A because the right-eye and left-eye deflecting zoom lens optical systems 134 and 136 have a smaller optical axis interval.

FIG. 21B is a schematic sectional view of a parallel binocular display similar to that in FIG. 20B, and here, through interpupillary distance adjustment, the left-eye display surface 14a and the left-eye eyepiece lens 20a are brought closer to the right-eye display surface 12a and the right-eye eyepiece lens 18a respectively, so that the interpupillary distance of the parallel binocular display equals the interval between the optical axes of the parallel binocular imaging system. This state is suitable for a display for children with smaller interpupillary distances. As a result of the distances between the optical axes of the parallel binocular imaging system and of the parallel binocular display system being made equal, the relationship between FIGS. 21A and 21B is similar to the relationship between FIGS. 13A and 13B, and the virtual-image display points 146a and 148a on the virtual images 12b and 14b of the right-eye and left-eye display surfaces 12a and 14a coincide. Their positions appear to be at the same distance as that of the object point 88 as the imaging target, and no sense of unnaturalness is produced. In this way, a sense of unnaturalness can be eliminated also through adjustment of the optical axis interval.

FIG. 21C is the same as FIG. 20C, and shows a case where, through interpupillary distance adjustment, the interpupillary distance has been increased, for example, for adults. In this case, as in Example 5, the central controller 80 controls the image processor 81 so as to shift the display points on the right-eye and left-eye display surfaces 12a and 14a, and thereby eliminates a sense of unnaturalness.

EXAMPLE 7

Figure 22A:
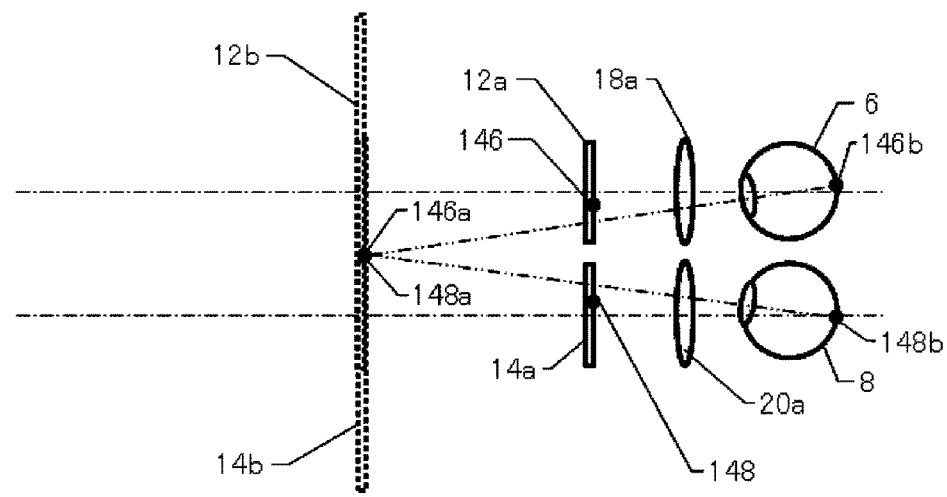
FIG. 22A is a schematic sectional view (a basic combination) of Example 7 embodying the present invention (Example 7)
Figure 22B:
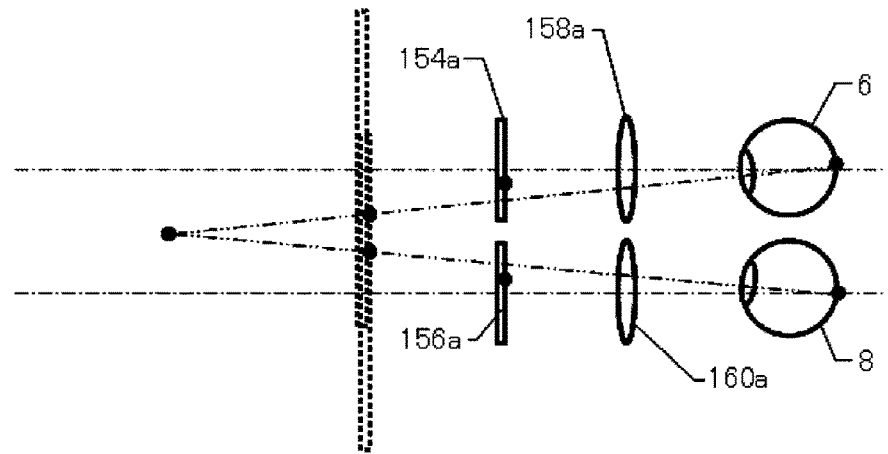
FIG. 22B is a schematic sectional view (another combination, with no shifting) of Example 7 embodying the present invention (Example 7)
Figure 22C:
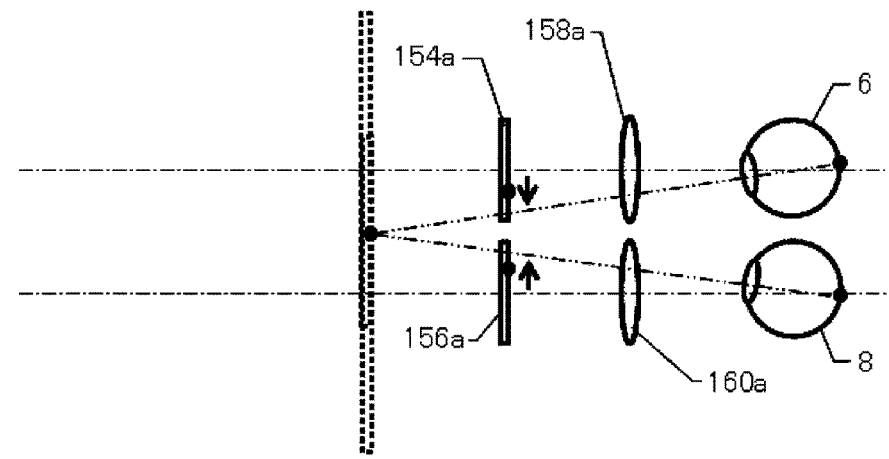
FIG. 22C is a schematic sectional view (another combination, with shifting) of Example 7 embodying the present invention (Example 7).

FIGS. 22A to 22C are schematic sectional views of Example 7 embodying the present invention. Example 7 has a parallel binocular imaging system and a parallel binocular display configured as separate units, and is suitable in cases where one of different types of parallel binocular imaging systems and one of different types of parallel binocular displays are combined together.

FIG. 22A shows a parallel binocular display used in a basic combination, and its configuration is the same as in FIG. 21B. However, here, the interpupillary distance is fixed at a small distance. In the basic combination of Example 7, the parallel binocular display in FIG. 22A is combined with the parallel binocular imaging system shown in FIG. 21A. This combination is equivalent to the relationship between FIGS. 21B and 21A, and thus produces no sense of unnaturalness.

FIG. 22B shows another parallel binocular display that can be combined with the parallel binocular imaging system shown in FIG. 21A. The optical axis interval of the parallel binocular display in FIG. 22B is equal to that of the parallel binocular imaging system, but here, right-eye and left-eye display surfaces 154a and 156a are located at positions far away from the right and left eyes 6 and 8, and right-eye and left-eye eyepiece lenses 158a and 160a have accordingly different optical systems. Thus, in this combination, the relationship between the parallel binocular imaging system and the parallel binocular display is similar to that between FIGS. 20A and 20B. Thus, as shown in FIG. 22C, correction as in FIG. 20C is performed to eliminate a sense of unnaturalness. To that end, whatever parallel binocular imaging system and parallel binocular display used hold information necessary for correction and communicate it to each other.

The various features of the examples described above provide their benefits without being limited to those particular embodiments.

For example, the various features of those examples which are configured as a vision aid system in which a binocular imaging system and a binocular display device are integrated together and which allows real-time viewing of the visual field before the eyes may be applied to a configuration where, as in Example 7, a binocular imaging system and a binocular display device are configured as separate units comprising a 3D camera and a 3D head-mounted display respectively. It is thereby possible to build a system that allows 3D movie content taken by the 3D camera to be viewed at different times and/or at different places through the 3D head-mounted display.

To follow is a comprehensive description of the various examples described above.

According to one aspect of the examples disclosed herein, a vision aid system is provided that includes: an imager which images a target that a user intends to see; an image processor which corrects an image obtained by the imager to suit the user's vision disorder; a display which displays the image from the image processor so that the user sees it; a light transmitter through which the user directly sees a target outside the display that the user intends to see; and a controller which controls the light transmitter in a manner corresponding to the image processing by the image processor. This makes it possible to match the image on the display with the target seen directly through the light transmitter.

According to a specific feature, the light transmitter is controlled according to the brightness of the display. According to another specific feature, the light transmitter can be controlled both according to the brightness of the display and irrespective of the brightness of the display. According to another specific feature, the light transmitter is light-shielded when the display is white-black reversed.

According to another specific feature, the image processor compensates for a pupil reaction. According to another specific feature, the controller which controls the light transmitter compensates for a pupil reaction. These features make possible control with a pupil reaction taken into consideration.

According to another aspect of the examples disclosed herein, a vision aid system is provided that includes: an imager which images a target that a user intends to see; an image processor which corrects an image obtained by the imager to suit the user's vision disorder; a display which displays the image from the image processor so that the user sees it; and a memory which stores preset information on correction in the image processor. Here, the preset information is definitively determined by averaging a plurality of values judged to be optimal. This makes it possible to determine appropriate preset values definitively. According to a specific feature, the preset information is stored separately for the right and left eyes.

According to another aspect of the examples disclosed herein, a vision aid system is provided that includes: an imager which images a target that a user intends to see; an image processor which corrects an image obtained by the imager to suit the user's vision disorder; and a display which displays the image from the image processor so that the user sees it. Here, the image processor can display an image on the display on an enlarged scale, and delays movement of the displayed image when enlargement higher than a predetermined magnification is performed. This alleviates the sense of unnaturalness felt in viewing an enlarged image.

According to another aspect of the examples disclosed herein, a vision aid system is provided that includes: an imager which images a target that a user intends to see; and a display which displays the image obtained by the imager so that the user sees it. Here, the optical axis of the imager and the optical axis of the display coincide with each other. This provides a vision aid system that is comfortable to see with. According to a specific feature, a controller is further included which displaces the optical axis of the imager and the optical axis of the display from each other. This makes it possible to cope with a variety of vision disorders.

According to another aspect of the examples disclosed herein, a vision aid system is provided that includes: a pair of imagers, one for each eye, which images a target that a user intends to see; and a pair of displays, one for each eye, which displays the images from the pair of imagers, respectively, so that the user sees them. Here, the pair of imagers and the pair of displays are arranged so as not to intercept outside the visual field of the two eyes. This makes it possible to obtain information outside the visual field effectively. According to a specific feature, each of the pair of imagers is bent inward of the two eyes. According to another specific feature, the pair of imagers are arranged so as not to protrude frontward.

According to another aspect of the examples disclosed herein, a vision aid system is provided that includes: an imager which images a target that a user intends to see; an image processor which corrects an image obtained by the imager to suit the user's vision disorder; a display which displays the image from the image processor so that the user sees it; a memory which stores a plurality of processing modes by the image processor; and a selector which selects among the plurality of processing modes. This makes it possible to select a processing mode that suits the circumstances of use.

According to a specific feature of the examples disclosed herein, a manual operation that is inappropriate for selection is restricted based on detection by a circumstance sensor which detects the circumstances of use. For example, when the circumstance sensor detects acceleration, an operation to select an image-enlarging mode is restricted. This helps avoid an accident or the like. In this configuration, the user may be notified that the manual operation is inappropriate. According to another feature, a processing mode of the memory is selected automatically based on detection by the circumstance sensor. This makes it possible to automatically select a processing mode that suits the circumstances of use.

According to a specific feature of the examples disclosed herein, the memory learns and stores a processing mode that suits the circumstances based on detection by the circumstance sensor at the time that a manual operation is done. This makes it possible to automatically select a processing mode of the memory based on what has been learned and stored and the corresponding detection by the circumstance sensor. Moreover, when a processing mode of the memory is selected automatically based on detection by the circumstance sensor, it is possible to judge based on what has been learned and stored whether the automatic selection is appropriate or not.

According to another aspect of the examples disclosed herein, a vision aid system is provided that includes: an imager which images a target that a user intends to see; an image processor which corrects an image obtained by the imager to suit the user's vision disorder; a display which displays the image from the image processor so that the user sees it; and a controller which reduces the frame rate of image display on the display when the image processor enlarges an image. This helps alleviate motion sickness or the like visually induced when an image is enlarged.

According to another aspect of the examples disclosed herein, a vision aid system is provided that includes: an imager which images a target that a user intends to see; an image processor which corrects an image obtained by the imager to suit the user's vision disorder; a display which displays the image from the image processor so that the user sees it; a circumstance sensor which detects the circumstances of use; and a controller which stops the display from changing display when the circumstance sensor detects minute vibrations. This helps alleviate motion sickness or the like visually induced by minute vibrations of an image.

According to another aspect of the examples disclosed herein, a vision aid system is provided that includes: an imager which images a target that a user intends to see; an image processor which corrects an image obtained by the imager to suit the user's vision disorder; a display which displays the image from the image processor so that the user sees it; a circumstance sensor which detects the circumstances of use; and a controller which changes the processing by the image processor based on detection by the circumstance sensor. This makes it possible to change display automatically according to the circumstances.

According to another aspect of the examples disclosed herein, a vision aid system is provided that includes: an imager which images a target that a user intends to see; an image processor which corrects an image obtained by the imager to suit the user's vision disorder; a display which displays the image from the image processor so that the user sees it; a circumstance sensor which detects the circumstances of use; a changer which changes the processing by the image processor; and a controller which effects an automatic return of the processing by the image processor to a standard state based on detection by the circumstance sensor. This makes it possible to automatically return from an image enlarging state for reading purposes to a real-scale state or a wide state for those with visual field constriction when, for example, the circumstance sensor detects acceleration resulting from the user starting to walk.

According to yet another aspect of the examples disclosed herein, a binocular display is provided that includes a binocular display system which receives image information from a binocular imaging system having mutually parallel optical axes and which has an optical axis interval equivalent to the optical axis interval of the binocular imaging system.

According to a specific feature, the binocular display provides a display virtual image at a distance equivalent to the standard subject distance of the binocular imaging system.

According to another specific feature, the binocular display has a dioptric power adjusting function.

According to another specific feature, the binocular display has an image enlarging function and an image reducing function.

According to another aspect of the examples disclosed herein, a binocular display is provided that includes: a binocular display system which receives image information from a binocular imaging system having mutually parallel optical axes and which has an optical axis interval different from the optical axis interval of the binocular imaging system; and an image shifting function based on a difference between the optical axis interval of the binocular imaging system and the optical axis interval of the binocular display system.

According to another aspect of the examples disclosed herein, a binocular display is provided that includes: a binocular display system having an optical axis interval adjusting function; and an image shifting function based on optical axis interval adjustment in the binocular display system.

According to another aspect of the examples disclosed herein, a binocular display is provided that includes: a binocular display system which receives image information from a binocular imaging system having mutually parallel optical axes and which has a display optical system different from the binocular imaging system; and an image shifting function based on a difference of the display optical system.

INDUSTRIAL APPLICABILITY

The present invention finds application in vision aid systems and binocular display apparatuses.

LIST OF REFERENCE SIGNS 22, 24, 26, 28 imager
50 image processor
12, 18, 14, 20 display
32, 26 light transmitter
54 controller for controlling light transmitters
16 controller for displacing optical axes
56 memory
22, 24, 26, 28 imager
50 image processor
12, 18, 14, 20 display
72 memory for storing processing modes
58, 74 selector
40, 44, 66, 70 circumstance sensor
74 controller for lowering a frame rate of image display
74 controller for stopping display from being changed
74 controller for changing processing by an image processor
74 controller for an automatic return of processing by an image processor to a standard state
24, 28, 134, 136 binocular imaging system
12a, 14a, 18a, 20a binocular display system
80, 81 image shifting function

The invention claimed is:

1. A binocular display apparatus comprising:
a binocular imaging system including a right-eye imaging optical system and a left-eye imaging optical system;
a binocular display system including a right-eye display configured to display image information taken by the right-eye imaging optical system and a left-eye display configured to display image information taken by the left-eye imaging optical system; and
correlating means for establishing a correlation between the binocular imaging system and the binocular display system, wherein
optical axes of the right-eye and left-eye imaging optical systems are parallel to each other with a first optical axis interval therebetween,
a second optical axis interval between optical axes of the right-eye and left-eye displays differs from the first optical axis interval, and
the correlating means has an image shifting function based on the difference between the first optical axis interval and the second optical axis interval with both the first optical axis interval and the second optical axis interval unchanged.

2. The binocular display apparatus of claim 1, wherein the correlating means establishes the correlation such that, when a subject taken by the binocular imaging system is displayed by the binocular display system, a convergence angle between right and left eyes seeing the subject displayed by the binocular display system is approximate to the convergence angle observed when the right and left eye really see the subject.

3. The binocular display apparatus of claim 1, wherein
the binocular display system is configured to provide a display virtual image at a distance equivalent to a standard subject distance of the binocular imaging system.

4. The binocular display apparatus of claim 1, wherein
the binocular display system has a dioptric power adjusting function.

5. The binocular display apparatus of claim 1, wherein
the binocular display system has at least one of an image enlarging function and an image reducing function.

6. The binocular display apparatus of claim 2, wherein
optical axes of the right-eye and left-eye imaging optical systems are parallel to each other,
the binocular display system has a display optical system different from the imaging optical systems of the binocular imaging system, and
the correlating means has an image shifting function based on a difference between the imaging optical system and the display optical system.

7. The binocular display apparatus of claim 1, further comprising:
an image processor configured to process the image information from the binocular imaging system; and
a memory configured to store preset information on correction in the image processor.

8. The binocular display apparatus of claim 7, wherein
the preset information is stored separately for right and left eyes.

9. The binocular display apparatus of claim 1, further comprising:
an image processor configured to be capable of displaying the image information from the binocular imaging system through the binocular display system on an enlarged scale and to correct movement of a displayed image when enlargement higher than a predetermined magnification is performed.

10. The binocular display apparatus of claim 1, further comprising:
a circumstance sensor configured to detect circumstances of use; and
a controller configured to stop the binocular display system from changing display when the circumstance sensor detects minute vibrations.

11. The binocular display apparatus of claim 9, wherein
the image processor is configured to correct movement of the displayed image by delaying the movement of the displayed image when enlargement higher than the predetermined magnification is performed.

12. The binocular display apparatus of claim 9, wherein
the image processor is configured to correct movement of the displayed image by reducing a frame rate of image display on the displays when enlargement higher than the predetermined magnification is performed.

13. The binocular display apparatus of claim 10, further comprising:
a processing controller configured to automatically change processing by the image processor based on detection by the circumstance sensor.

14. The binocular display apparatus of claim 13, wherein
the processing controller is configured to effect an automatic return of the processing by the image processor to a standard state based on the detection by the circumstance sensor.

* * * * *